United States Patent [19]

Flaugh et al.

[11] Patent Number: 5,932,739
[45] Date of Patent: Aug. 3, 1999

[54] SUBSTITUTED 1,2,3,4-TETRAHYDRO-2-DIBENZOFURANAMINES AND 2-AMINOCYCLOHEPTA[6,7-B]BENZOFURANS

[75] Inventors: Michael E. Flaugh; Anton D. Kiefer, Jr., both of Indianapolis, Ind.

[73] Assignee: Eli Lilly and Company, Indianapolis, Ind.

[21] Appl. No.: 09/089,745

[22] Filed: Jun. 3, 1998

Related U.S. Application Data

[62] Division of application No. 08/918,155, Aug. 25, 1997, Pat. No. 5,846,995.

[60] Provisional application No. 60/024,745, Aug. 28, 1996.

[51] Int. Cl.⁶ .......................... C07D 405/12; A61K 31/44

[52] U.S. Cl. ........................ 546/284.1; 514/337; 514/468; 549/461

[58] Field of Search ........................ 546/284.1; 549/461; 514/337, 468

[56] References Cited

U.S. PATENT DOCUMENTS 4,668,690  5/1987  Shutske ................................... 514/320

*Primary Examiner*—Alan L. Rotman
*Assistant Examiner*—Charanjit S. Aulakh
*Attorney, Agent, or Firm*—Robert D. Titus

[57] ABSTRACT

The invention provides substituted-2-amino-1,2,3,4-tetrahydrodibenzofurans and 2-aminocyclohepta[b]benzofurans useful as 5-$HT_{1F}$ agonists.

12 Claims, No Drawings

SUBSTITUTED 1,2,3,4-TETRAHYDRO-2-DIBENZOFURANAMINES AND 2-AMINOCYCLOHEPTA[6,7-B]BENZOFURANS

CROSS-REFERENCE

This application is a divisional of application Ser. No. 08/918,155, filed Aug. 25, 1997, U.S. Pat. No. 5,846,995 which is a provisional of Ser. No. 60/024,745 filed Aug. 28, 1996.

BACKGROUND OF THE INVENTION

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. The high affinity of sumatriptan at this subtype, $K_i$=23 nM, suggests a role of the 5-HT$_{1F}$ receptor in migraine.

This invention provides novel 5-HT$_{1F}$ agonists which inhibit peptide extravasation due to stimulation of the trigeminal ganglia, and are therefore useful for the treatment and prevention of migraine and associated disorders.

SUMMARY OF THE INVENTION

The present invention provides novel 8-substituted-1,2,3,4-tetrahydro-2-dibenzofuranamines and 9-substituted-2-aminocyclohepta[b]benzofurans of Formula I:

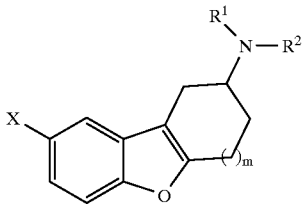

wherein:
R$^1$ and R$^2$ are independently hydrogen, C$_1$–C$_4$ alkyl, benzyl, or α-methyl-4-nitrobenzyl;
X is nitro, halo, —OH, —NH$_2$, —CN, —NHC(O)R$^3$, —C(O)R$^6$, —NHSO$_2$R$^7$, or —SO$_2$NHR$^{10}$;
R$^3$ is C$_1$–C$_6$ alkyl, C$_2$–C$_6$ alkenyl, C$_3$–C$_8$ cycloalkyl, phenyl, substituted phenyl, naphthyl, phenyl(C$_1$–C$_4$ alkylene), thienylmethyl, or a heterocycle;
R$^6$ is hydroxy, amino, C$_1$–C$_6$ alkoxy, benzyloxy, phenoxy, or —NHR$^8$;
R$^7$ is C$_1$–C$_6$ alkyl, phenyl or phenyl monosubstituted with halo or C$_1$–C$_4$ alkyl;
R$^8$ is C$_1$–C$_6$ alkyl, C$_2$–C$_6$ alkenyl, C$_3$–C$_8$ cycloalkyl, phenyl, substituted phenyl, naphthyl, or a heterocycle; and
R$^{10}$ is C$_1$–C$_6$ alkyl, phenyl or phenyl monosubstituted with halo or C$_1$–C$_4$ alkyl;
m is 1 or 2; and pharmaceutically acceptable salts thereof;

A further embodiment of this invention is a method for increasing activation of the 5-HT$_{1F}$ receptor by administering a compound of Formula I.

Activation of the 5-HT$_{1F}$ receptor provides a method for treating a variety of disorders which have been linked to decreased neurotransmission of serotonin in mammals. Included among these disorders are depression, migraine pain, prevention of migraine, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, allergic rhinitis, cold symptoms, pain, or trichotillomania. Any of these methods employ a compound of Formula I.

In addition, this invention provides pharmaceutical formulations comprising an effective amount for activation of the 5-HT$_{1F}$ receptor of a compound of Formula I, in combination with a suitable pharmaceutical carrier, diluent, or excipient.

This invention also provides the use of a compound of Formula I for the manufacture of a medicament for the prevention or treatment of migraine and associated disorders. Additionally, this invention provides a pharmaceutical formulation adapted for the prevention or treatment of migraine containing a compound of Formula I. Furthermore, this invention includes a method for the prevention or treatment of migraine which comprises administering an effective amount of a compound of Formula I.

DETAILED DESCRIPTION OF THE INVENTION

The general chemical terms used in the formulae above have their usual meanings. For example, the term "alkyl"

include such groups as methyl, ethyl, n-propyl, isopropyl, n-butyl, isobutyl, sec-butyl, tert-butyl, 1-pentyl, 2-pentyl-, 3-pentyl-, neopentyl, hexyl, and the like. The term "alkoxy" includes methoxy, ethoxy, isopropoxy, butoxy, tert-butoxy, hexyloxy, and the like. The term "alkylthio" includes methylthio, ethylthio, isopropylthio, butylthio, tert-butylthio, hexylthio, and the like. The term "alkenyl" includes allyl, 1-buten-4-yl, 2-methyl-1-buten-4-yl, 2-buten-4-yl, 1-penten-5-yl, 4-methyl-2-penten-5-yl, 2-penten-5-yl, 3-penten-5-yl, 1-hexen-6-yl, 2-hexen-6-yl, 3-hexen-6-yl, 4-hexen-6-yl and the like. The term "acyl" includes formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "phenyl($C_1$–$C_4$ alkylene)" includes such groups as benzyl, phenethyl, 1-phenyl-2-methylpropyl, phenpropyl and phenbutyl. The term "($C_1$–$C_4$ alkyl)sulfonyl" includes methanesulfonyl, ethanesulfonyl, propanesulfonyl, isopropanesulfonyl, butanesulfonyl and the like. The term "halo" includes fluoro, chloro, bromo and iodo.

The term "substituted phenyl" is taken to mean a phenyl group substituted with one substituent selected from the group consisting of halo, $C_1$–$C_4$ alkyl, $C_1$–$C_4$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sulfonyl, or two to three substituents independently selected from the group consisting of halo, nitro, $C_1$–$C_4$ alkyl, or $C_1$–$C_4$ alkoxy.

The term "heterocycle" is taken to mean optionally substituted furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, isoquinolinyl, benzofuranyl, benzo[b]thienyl, or 1H-indolyl bonded through any available ring carbon atom. Optional substitution of these heterocycles with 1–3 substituents, selected from the group consisting of halo, $C_1$–$C_4$ alkyl or $C_1$–$C_4$ alkoxy, may occur on available ring carbon atoms.

The term "α-methyl-4-nitrobenzyl" is taken to mean the racemic form as well as the individual R-(+)- and S-(−)-enantiomers.

The term "alkoxycarbonyl" is taken to mean an ester moiety whose oxygen atom bears a $C_1$–$C_4$ alkyl or $C_3$–$C_6$ cycloalkyl.

The term "aryloxycarbonyl" is taken to mean an ester moiety whose oxygen atom bears a phenyl, benzyl, naphthyl, substituted phenyl or heterocycle group.

The compounds of the present invention possess an asymmetric carbon labelled with an asterisk in the following formula:

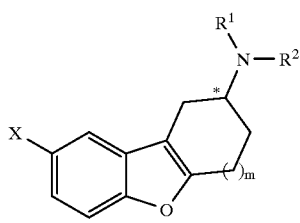

As such, each of the compounds of the present invention exists not only as the racemate but as individual d- and l-enantiomers as well:

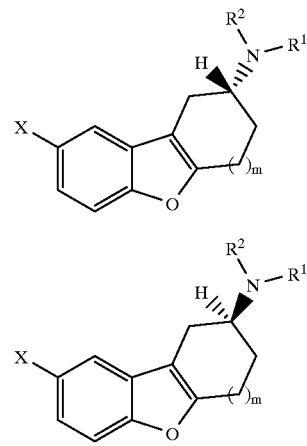

The compounds of the present invention include not only the dl-racemates, but also their respective optically active d- and l-enantiomers. Particularly useful chiral intermediates for the preparation of the compounds of this invention are those compounds where X is bromo, or —$NH_2$.

While all of the compounds of this invention are useful as 5-$HT_{1F}$ agonists, certain classes are preferred. The following paragraphs describe such preferred classes.

aa) $R^1$ is hydrogen;
ab) $R^1$ is $C_1$–$C_6$ alkyl;
ac) $R^1$ is ethyl;
ad) $R^1$ is methyl;
ae) $R^2$ is hydrogen;
af) $R^2$ is $C_1$–$C_6$ alkyl;
ag) $R^2$ is ethyl;
ah) $R^2$ is methyl;
ai) X is —OH;
aj) X is —NHC(O)$R^3$;
ak) X is —C(O)$R^6$;
al) X is —NHSO$_2$$R^7$;
am) X is —SO$_2$NH$R^{10}$;
an) $R^3$ is $C_1$–$C_6$ alkyl;
ao) $R^3$ is $C_2$–$C_6$ alkenyl;
ap) $R^3$ is $C_3$–$C_6$ cycloalkyl;
aq) $R^3$ is cyclobutyl;
ar) $R^3$ is cyclopropyl;
as) $R^3$ is phenyl;
at) $R^3$ is phenyl monosubstituted with halo;
au) $R^3$ is phenyl monosubstituted with fluoro;
av) $R^3$ is phenyl monosubstituted with chloro;
aw) $R^3$ is 4-fluorophenyl;
ax) $R^3$ is 2-chlorophenyl;
ay) $R^3$ is phenyl monosubstituted with $C_1$–$C_4$ alkoxy;
az) $R^3$ is phenyl monosubstituted with $C_1$–$C_4$ alkyl;
ba) $R^3$ is phenyl monosubstituted with methyl;
bb) $R^3$ is 2-methylphenyl;
bc) $R^3$ is phenyl disubstituted with halo;
bd) $R^3$ is 2-chloro-4-fluorophenyl;
be) $R^3$ is a heterocycle;
bf) $R^3$ is furyl optionally substituted with $C_1$–$C_4$ alkyl, $C_1$–$C_4$ alkoxy, or halo;
bg) $R^3$ is 2-furyl;
bh) $R^3$ is 3-furyl;
bi) $R^3$ is thienyl optionally substituted with $C_1$–$C_4$ alkyl or $C_1$–$C_4$ alkoxy;
bj) $R^3$ is 2-thienyl;
bk) $R^3$ is 3-thienyl;
bl) $R^3$ is pyridinyl optionally substituted with halo, $C_1$–$C_4$ alkyl or $C_1$–$C_4$ alkoxy;

bm) R³ is 3-pyridinyl;
bn) R³ is 4-pyridinyl;
bo) R³ is 6-halo-3-pyridinyl;
bp) R⁶ is hydroxy;
bq) R⁶ is $C_1$–$C_6$ alkoxy;
br) R⁶ is benzyloxy;
bs) R⁶ is phenoxy;
bt) R⁶ is —NHR⁸;
bu) R⁶ is —NHR⁸ where R⁸ is $C_1$–$C_6$ alkyl;
bv) R⁶ is —NHR⁸ where R⁸ is phenyl;
bw) R⁶ is —NHR⁸ where R⁸ is substituted phenyl;
bx) R⁶ is —NHR⁸ where R⁸ is a heterocycle;
by) R⁷ is dimethylamino;
bz) R⁷ is $C_1$–$C_6$ alkyl;
ca) R⁷ is phenyl;
cb) R⁷ is substituted phenyl;
cc) m is 1;
cd) m is 2;
ce) The compound is a racemate;
cf) The compound is the 1-enantiomer;
cg) The compound is the d-enantiomer;
ch) The compound is a free base;
ci) The compound is a salt;
cj) The compound is the hydrochloride salt;
ck) The compound is the fumarate salt;
ci) The compound is the oxalate salt.

It will be understood that the above classes may be combined to form additional preferred classes.

The compounds of this invention are useful in a method for increasing activation of the 5-HT$_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The following group is illustrative of compounds contemplated within the scope of this invention:

N,N-dimethyl-8-hydroxy-1,2,3,4-tetrahydro-2-dibenzofuranamine

N,N-dimethyl-8-amino-1,2,3,4-tetrahydro-2-dibenzofuranamine hydrochloride

N,N-diethyl-8-fluoro-1,2,3,4-tetrahydro-2-dibenzofuranamine

N-ethyl-8-chloro-1,2,3,4-tetrahydro-2-dibenzofuranamine sulfate

N-methyl-N-benzyl-8-bromo-1,2,3,4-tetrahydro-2-dibenzofuranamine

N,N-dipropyl-8-iodo-1,2,3,4-tetrahydro-2-dibenzofuranamine hydrobromide

N-(N,N-dimethyl-1,2,3,4-tetrahydro-2-aminodibenzo-fur-8-yl)acetamide

N-(N,N-dimethyl-1,2,3,4-tetrahydro-2-aminodibenzo-fur-8-yl)propanamide (−)-N-(N,N-dimethyl-1,2,3,4-tetrahydro-2-aminodibenzofur-8-yl)hexanamide phosphate N-(N,N-dimethyl-1,2,3,4-tetrahydro-2-aminodibenzo-fur-8-yl)acrylamide N-(N,N-dimethyl-1,2,3,4-tetrahydro-2-aminodibenzo-fur-8-yl)cyclobutanamide acetate N-(N,N-dimethyl-1,2,3,4-tetrahydro-2-aminodibenzo-fur-8-yl)cyclohexanamide N-(N,N-dimethyl-1,2,3,4-tetrahydro-2-aminodibenzo-fur-8-yl)benzamide N-(N-methyl-N-isopropyl-1,2,3,4-tetrahydro-2-aminodibenzofur-8-yl)naphth-1-ylamide decanoate N-(N,N-dimethyl-1,2,3,4-tetrahydro-2-aminodibenzo-fur-8-yl)naphth-2-ylamide N-(N,N-dimethyl-1,2,3,4-tetrahydro-2-aminodibenzo-fur-8-yl)phenylacetamide N-(N,N-dimethyl-1,2,3,4-tetrahydro-2-aminodibenzo-fur-8-yl)-3-methoxythien-2-ylacetamide N-(N,N-dimethyl-1,2,3,4-tetrahydro-2-aminodibenzo-fur-8-yl)pyrrole-2-carboxamide N-(N,N-dimethyl-1,2,3,4-tetrahydro-2-aminodibenzo-fur-8-yl)-5-methyloxazole-2-carboxamide acrylate N-(N,N-dimethyl-1,2,3,4-tetrahydro-2-aminodibenzo-fur-8-yl)oxazole-4-carboxamide N-(N,N-dimethyl-1,2,3,4-tetrahydro-2-aminodibenzo-fur-8-yl)isoxazole-3-carboxamide N-(N,N-dimethyl-1,2,3,4-tetrahydro-2-aminodibenzo-fur-8-yl)pyrazole-3-carboxamide formate N-(1,2,3,4-tetrahydro-2-aminodibenzofur-8-yl)pyra-zole-4-carboxamide N-(N,N-dimethyl-1,2,3,4-tetrahydro-2-aminodibenzo-fur-8-yl)imidazole-2-carboxamide malonate N-(N,N-dimethyl-1,2,3,4-tetrahydro-2-aminodibenzo-fur-8-yl)imidazole-4-carboxamide N-(N,N-dimethyl-1,2,3,4-tetrahydro-2-aminodibenzo-fur-8-yl)-1,2,3-triazole-4-carboxamide fumarate N-(N,N-dimethyl-1,2,3,4-tetrahydro-2-aminodibenzo-fur-8-yl)-5-chloropyrimidine-2-carboxamide N-(N,N-dimethyl-1,2,3,4-tetrahydro-2-aminodibenzo-fur-8-yl)pyrimidine-4-carboxamide butyne-1,4-dioate N-(N,N-dimethyl-1,2,3,4-tetrahydro-2-aminodibenzo-fur-8-yl)pyrazine-2-carboxamide benzoate N-(N-hexyl-1,2,3,4-tetrahydro-2-aminodibenzofur-8-yl)pyridazine-3-carboxamide N-(N,N-dimethyl-1,2,3,4-tetrahydro-2-aminodibenzo-fur-8-yl)pyridazine-4-carboxamide 4-chlorobenzoate N-(N-methyl-N-phenethyl-1,2,3,4-tetrahydro-2-aminodibenzofur-8-yl)quinoline-2-carboxamide phthalate N-(N-isobutyl-1,2,3,4-tetrahydro-2-aminodibenzofur-8-yl)quinoline-4-carboxamide p-toluenesulfonate N-(N,N-dimethyl-1,2,3,4-tetrahydro-2-aminodibenzo-fur-8-yl)quinoline-5-carboxamide methanesulfonate N-(N,N-dimethyl-1,2,3,4-tetrahydro-2-aminodibenzo-fur-8-yl)isoquinoline-1-carboxamide dichloroacetate N-(N,N-dimethyl-1,2,3,4-tetrahydro-2-aminodibenzo-fur-8-yl)isoquinoline-3-carboxamide trifluoroacetate N-(N,N-dimethyl-1,2,3,4-tetrahydro-2-aminodibenzo-fur-8-yl)benzo[b]furan-2-carboxamide citrate N-(N,N-dimethyl-1,2,3,4-tetrahydro-2-aminodibenzo-fur-8-yl)benzo[b]furan-3-carboxamide tartrate (+)-N-(N,N-dimethyl-1,2,3,4-tetrahydro-2-aminodibenzofur-8-yl)benzo[c]furan-4-carboxamide N-(N-methyl-N-butyl-1,2,3,4-tetrahydro-2-aminodibenzofur-8-yl)-5-bromobenzo[b]thien-2-carboxamide N-(N,N-dimethyl-1,2,3,4-tetrahydro-2-aminodibenzo-fur-8-yl)benzo[b]thien-3-carboxamide (−)-N-(N,N-dimethyl-1,2,3,4-tetrahydro-2-aminodibenzofur-8-yl)benzo[c]thien-4-carboxamide hippurate N-(N,N-dimethyl-1,2,3,4-tetrahydro-2-aminodibenzo-fur-8-yl)benzo[b]thien-6-carboxamide naphthalene-1-sulfonate N-(N,N-dimethyl-1,2,3,4-tetrahydro-2-aminodibenzo-fur-8-yl)-6-ethoxyindole-2-carboxamide N-(N,N-dimethyl-1,2,3,4-tetrahydro-2-aminodibenzo-fur-8-yl)-7-fluoroindole-3-carboxamide N-(N,N-dimethyl-1,2,3,4-tetrahydro-2-aminodibenzo-fur-8-yl)indole-5-carboxamide N'-methyl-N,N-dimethyl-1,2,3,4-tetrahydro-2-dibenzofuranamine-8-carboxamide N'-isobutyl-N,N-dimethyl-1,2,3,4-tetrahydro-2-dibenzofuranamine-8-carboxamide N'-hexyl-N,N-dimethyl-1,2,3,4-tetrahydro-2-dibenzofuranamine-8-carboxamide N'-propenyl-1,2,3,4-tetrahydro-2-dibenzofuranamine-8-carboxamide N'-cyclopropyl-N-methyl-N-benzyl-1,2,3,4-tetrahydro-2-dibenzofuranamine-8-carboxamide (+)-N'-cyclohexyl-N,N-dimethyl-1,2,3,4-tetrahydro-2-dibenzofuranamine-8-carboxamide N'-phenyl-N,N-dimethyl-1,2,3,4-tetrahydro-2-dibenzofuranamine-8-carboxamide N'-(4-fluorophenyl)-N-butyl-N-ethyl-1,2,3,4-tetrahydro-2-dibenzofuranamine-8-carboxamide N'-(naphth-1-yl)-N,N-dimethyl-1,2,3,4-tetrahydro-2-dibenzofuranamine-8-carboxamide N'-(fur-2-yl)-N,N-dimethyl-1,2,3,4-tetrahydro-2-dibenzofuranamine-8-carboxamide N'-(thien-3-yl)-N,N-dimethyl-1,2,3,4-tetrahydro-2-dibenzofuranamine-8-carboxamide N'-(pyridin-4-yl)-N,N-dimethyl-1,2,3,4-tetrahydro-2-dibenzofuranamine-8-carboxamide N'-(6-chloropyridin-3-yl)-N,N-dimethyl-1,2,3,4-tetrahydro-2-dibenzofuranamine-8-carboxamide N'-(pyrrol-2-yl)-N,N-dimethyl-1,2,3,4-tetrahydro-2-dibenzofuranamine-8-carboxamide N'-(oxazol-4-yl)-N,N-dimethyl-1,2,3,4-tetrahydro-2-dibenzofuranamine-8-carboxamide N'-(isoxazol-3-yl)-N,N-dimethyl-1,2,3,4-tetrahydro-2-dibenzofuranamine-8-carboxamide N'-(pyrazol-3-yl)-N,N-dimethyl-1,2,3,4-tetrahydro-2-dibenzofuranamine-8-carboxamide N'-(imidazol-2-yl)-N,N-dimethyl-1,2,3,4-tetrahydro-2-dibenzofuranamine-8-carboxamide N'-(triazol-4-yl)-N,N-dimethyl-1,2,3,4-tetrahydro-2-dibenzofuranamine-8-carboxamide N'-(pyrimidin-2-yl)-N,N-dimethyl-1,2,3,4-tetrahydro-2-dibenzofuranamine-8-carboxamide N'-(pyrazin-2-yl)-N,N-dimethyl-1,2,3,4-tetrahydro-2-dibenzofuranamine-8-carboxamide N'-(pyridazin-4-yl)-N,N-dimethyl-1,2,3,4-tetrahydro-2-dibenzofuranamine-8-carboxamide N'-(quinolin-3-yl)-N,N-dimethyl-1,2,3,4-tetrahydro-2-dibenzofuranamine-8-carboxamide N'-(isoquinolin-5-yl)-N,N-dimethyl-1,2,3,4-tetra-hydro-2-dibenzofuranamine-8-carboxamide N'-(benzofur-2-yl)-N,N-dimethyl-1,2,3,4-tetrahydro-2-dibenzofuranamine-8-carboxamide N'-(benzo[b]thien-6-yl)-N,N-dimethyl-1,2,3,4-tetrahydro-2-dibenzofuranamine-8-carboxamide N'-(indol-2-yl)-N,N-dimethyl-1,2,3,4-tetrahydro-2-dibenzofuranamine-8-carboxamide N-(N,N-dimethyl-1,2,3,4-tetrahydro-2-aminodibenzo-fur-8-yl)methanesulfonamide N-(N,N-dimethyl-1,2,3,4-tetrahydro-2-aminodibenzo-fur-8-yl)ethanesulfonamide N-(N,N-dimethyl-1,2,3,4-tetrahydro-2-aminodibenzo-fur-8-yl)benzenesulfonamide N-(N,N-dimethyl-1,2,3,4-tetrahydro-2-aminodibenzo-fur-8-yl)-3-chlorobenzenesulfonamide N-(N,N-dimethyl-1,2,3,4-tetrahydro-2-aminodibenzo-fur-8-yl)-4-methylbenzenesulfonamide N,N-dimethyl-9-hydroxy-2-aminocyclohepta[b]ben-zofuran N,N-dimethyl-9-amino-2-aminocyclohepta[b]benzofuran hydrochloride N,N-diethyl-9-fluoro-2-aminocyclohepta[b]benzofuran N-ethyl-9-chloro-2-aminocyclohepta[b]benzofuran sulfate N-methyl-N-benzyl-9-bromo-2-aminocyclohepta[b]benzofuran N,N-dipropyl-9-iodo-2-aminocyclohepta[b]benzofuran hydrobromide N-(N,N-dimethyl-2-aminocyclohepta[b]benzofur-9-yl)acetamide N-(N,N-dimethyl-2-aminocyclohepta[b]benzofur-9-yl)propanamide (−)-N-(N,N-dimethyl-2-aminocyclohepta[b]benzofur-9-yl)hexanamide phosphate N-(N,N-dimethyl-2-aminocyclohepta[b]benzofur-9-yl)acrylamide N-(N,N-dimethyl-2-aminocyclohepta[b]benzofur-9-yl)cyclobutanamide acetate N-(N,N-dimethyl-2-aminocyclohepta[b]benzofur-9-yl)cyclohexanamide N-(N,N-dimethyl-2-aminocyclohepta[b]benzofur-9-yl)benzamide N-(N-methyl-N-isopropyl-2-aminocyclohepta[b]ben-zofur-9-yl)naphth-1-ylamide decanoate N-(N,N-dimethyl-2-aminocyclohepta[b]benzofur-9-yl)naphth-2-ylamide N-(N,N-dimethyl-2-aminocyclohepta[b]benzofur-9-yl)phenylacetamide N-(N,N-dimethyl-2-aminocyclohepta[b]benzofur-9-yl)thien-2-ylacetamide N-(N,N-dimethyl-2-aminocyclohepta[b]benzofur-9-yl)pyrrole-2-carboxamide N-(N,N-dimethyl-2-aminocyclohepta[b]benzofur-9-yl)oxazole-2-carboxamide acrylate N-(N,N-dimethyl-2-aminocyclohepta[b]benzofur-9-yl)2-propyloxazole-4-carboxamide N-(N,N-dimethyl-2-aminocyclohepta[b]benzofur-9yl)isoxazole-3-carboxamide N-(N,N-dimethyl-2-aminocyclohepta[b]benzofur-9-yl)pyrazole-3-carboxamide formate N-(2-aminocyclohepta[b]benzofur-9-yl)pyrazole-4-carboxamide N-(N,N-dimethyl-2-aminocyclohepta[b]benzofur-9-yl) imidazole-2-carboxamide malonate N-(N,N-dimethyl-2-aminocyclohepta[b]benzofur-9-yl) imidazole-4-carboxamide N-(N,N-dimethyl-2-aminocyclohepta[b]benzofur-9-yl)-1,2,4-triazole-3-carboxamide fumarate N-(N,N-dimethyl-2-aminocyclohepta[b]benzofur-9-yl) pyrimidine-2-carboxamide N-(N,N-dimethyl-2-aminocyclohepta[b]benzofur-9-yl) pyrimidine-4-carboxamide butyne-1,4-dioate N-(N-isopropyl-N-benzyl-2-aminocyclohepta[b]benzofur-9-yl)pyrazine-2-carboxamide benzoate N-(N,N-dimethyl-2-aminocyclohepta[b]benzofur-9-yl) pyridazine-3-carboxamide N-(2-aminocyclohepta[b]benzofur-9-yl)pyridazine-4-carboxamide 4-chlorobenzoate N-(N-methyl-N-phenethyl-2-aminocyclohepta[b]benzo-fur-9-yl)quinoline-2-carboxamide phthalate N-(N,N-dimethyl-2-aminocyclohepta[b]benzofur-9-yl) quinoline-4-carboxamide p-toluenesulfonate N-(N,N-dibutyl-2-aminocyclohepta[b]benzofur-9-yl)2-methylquinoline-6-carboxamide methanesulfonate N-(N,N-dimethyl-2-aminocyclohepta[b]benzofur-9-yl) isoquinoline-1-carboxamide trifluoromethanesulfonate N-(N,N-dimethyl-2-aminocyclohepta[b]benzofur-9-yl) isoquinoline-3-carboxamide trifluoroacetate N-(N,N-dimethyl-2-aminocyclohepta[b]benzofur-9-yl) isoquinoline-6-carboxamide citrate N-(N,N-dimethyl-2-aminocyclohepta[b]benzofur-9-yl) benzo[b]furan-2-carboxamide mandelate N-(N,N-dimethyl-2-aminocyclohepta[b]benzofur-9-yl)5-fluorobenzo[b]furan-3-carboxamide tartrate (+)-N-(N,N-dibenzyl-2-aminocyclohepta[b]benzofur-9-yl) benzo[b]furan-4-carboxamide N-(N,N-dimethyl-2-aminocyclohepta[b]benzofur-9-yl) benzo[b]thien-2-carboxamide N-(N,N-dimethyl-2-aminocyclohepta[b]benzofur-9-yl) benzo[b]thien-3-carboxamide (−)-N-(N,N-dimethyl-2-aminocyclohepta[b]benzofur-9-yl) benzo[b]thien-4-carboxamide hippurate N-(N-isopropyl-2-aminocyclohepta[b]benzofur-9-yl)-4-methoxyindole-2-carboxamide N-(N,N-dimethyl-2-aminocyclohepta[b]benzofur-9-yl) indole-3-carboxamide N-(N,N-dimethyl-2-aminocyclohepta[b]benzofur-9-yl) indole-7-carboxamide N'-methyl-N,N-dimethyl-2-aminocyclohepta[b]benzofur-9-ylcarboxamide N'-ethyl-N,N-dimethyl-2-aminocyclohepta[b]benzofur-9-ylcarboxamide N'-isopropyl-N,N-dimethyl-2-aminocyclohepta[b]benzofur-9-ylcarboxamide N'-propenyl-N,N-dimethyl-2-aminocyclohepta[b]benzo-fur-9-ylcarboxamide N'-cyclopropyl-N,N-dimethyl-2-aminocyclohepta[b] benzofur-9-ylcarboxamide (+)-N'-cyclohexyl-N,N-dimethyl-2-aminocyclohepta[b] benzofur-9-ylcarboxamide N'-phenyl-N,N-dimethyl-2-aminocyclohepta[b]benzofur-9-ylcarboxamide N'-(4-fluorophenyl)-N,N-dimethyl-2-aminocyclohepta[b] benzofur-9-ylcarboxamide N'-(naphth-1-yl)-N,N-dimethyl-2-aminocyclohepta[b] benzofur-9-ylcarboxamide N'-(fur-2-yl)-N,N-dimethyl-2-aminocyclohepta[b]benzofur-9-ylcarboxamide N'-(thien-3-yl)-N,N-dimethyl-2-aminocyclohepta[b] benzofur-9-ylcarboxamide N'-(pyridin-4-yl)-N,N-dimethyl-2-aminocyclohepta[b] benzofur-9-ylcarboxamide N'-(6-chloropyridin-3-yl)-N,N-dimethyl-2-aminocyclohepta[b]benzofur-9-ylcarboxamide N'-(pyrrol-2-yl)-N,N-dimethyl-2-aminocyclohepta[b] benzofur-9-ylcarboxamide N'-(oxazol-4-yl)-N,N-dimethyl-2-aminocyclohepta[b] benzofur-9-ylcarboxamide N'-(isoxazol-3-yl)-N,N-dimethyl-2-aminocyclohepta[b] benzofur-9-ylcarboxamide N'-(pyrazol-3-yl)-N,N-dimethyl-2-aminocyclohepta[b] benzofur-9-ylcarboxamide N'-(imidazol-2-yl)-N,N-dimethyl-2-aminocyclohepta[b] benzofur-9-ylcarboxamide N'-(triazol-4-yl)-N,N-dimethyl-2-aminocyclohepta[b] benzofur-9-ylcarboxamide N'-(pyrimidin-2-yl)-N,N-dimethyl-2-aminocyclohepta[b] benzofur-9-ylcarboxamide N'-(pyrazin-2-yl)-N,N-dimethyl-2-aminocyclohepta[b] benzofur-9-ylcarboxamide N'-(pyridazin-4-yl)-N,N-dimethyl-2-aminocyclohepta[b] benzofur-9-ylcarboxamide N'-(quinolin-3-yl)-N,N-dimethyl-2-aminocyclohepta[b] benzofur-9-ylcarboxamide N'-(isoquinolin-5-yl)-N,N-dimethyl-2-aminocyclohepta[b] benzofur-9-ylcarboxamide N'-(benzofur-2-yl)-N,N-dimethyl-2-aminocyclohepta[b] benzofur-9-ylcarboxamide N'-(benzo[b]thien-6-yl)-N,N-dimethyl-2-aminocyclohepta [b]benzofur-9-ylcarboxamide N'-(indol-2-yl)-N,N-dimethyl-2-aminocyclohepta[b] benzofur-9-ylcarboxamide N-(N,N-dimethyl-2-aminocyclohepta[b]benzofur-9-yl) methanesulfonamide N-(N,N-dimethyl-2-aminocyclohepta[b]benzofur-9-yl) ethanesulfonamide N-(N,N-dimethyl-2-aminocyclohepta[b]benzofur-9-yl) benzenesulfonamide N-(N,N-dimethyl-2-aminocyclohepta[b]benzofur-9-yl)-3-chlorobenzenesulfonamide N-(N,N-dimethyl-2-aminocyclohepta[b]benzofur-9-yl)-4-methylbenzenesulfonamide The compounds of the present invention where X is nitro, cyano, C(O)R$^6$, or —SO$_2$NHR$^{10}$ are prepared by the novel method described in Synthetic Scheme I. X' is nitro, cyano, C(O)R$^6$, or —SO$_2$NR$^9$R$^{10}$; R$^{1*}$ and R$^{2*}$ are independently C$_1$–C$_4$ alkyl, benzyl or, together with the nitrogen to which they are attached, form a phthalimido group; R$^6$ is hydroxy, C$_1$–C$_6$ alkoxy, benzyloxy, or phenoxy; R$^9$ is a nitrogen protecting group; and R$^{10}$ and m are as previously defined. Nitrogen protecting groups useful for these reactions are well known to the skilled artisan (Greene, *Protective Groups in Organic Synthesis*, Second Edition, Wiley Interscience, New York (1991)). Preferred protecting groups are benzyl and 4-methoxyben-zyl.

Synthetic Scheme I

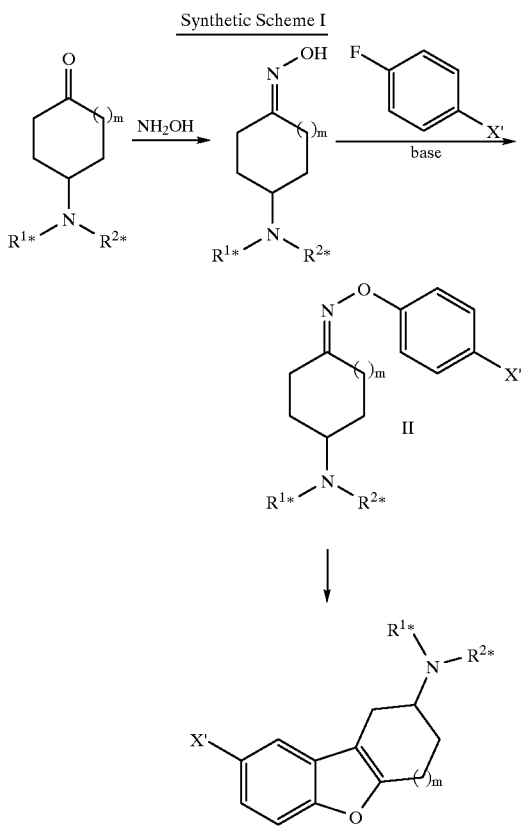

An appropriate 4-aminoketone and hydroxylamine hydrochloride are combined in an appropriate solvent, typically a lower alkanol such as methanol or ethanol. The resulting mixture is treated with a suitable base, typically pyridine or triethylamine, and the reaction mixture heated to reflux until all of the starting aminoketone has reacted. The resulting oxime may then be used directly or purified by crystallization or chromatography. The resulting oxime and substituted fluorobenzene are combined in an appropriate solvent, for example tetrahydrofuran, dimethylformamide or N-methylpyrrolidinone. This mixture is then treated with a suitable base, such as sodium or potassium hydride, and the reaction mixture warmed in the range of from about 50° C. to about 70° C. until the oxime is consumed. The use of potassium hydride in tetrahydrofuran is preferred. Preferably, this step is performed in the presence of a crown ether, typically 18-crown-6. The resulting O-substituted oxime (II) is isolated by normal extractive workup and may be purified, if necessary or desired, by crystallization or chromatography. The O-substituted oxime is then treated with an acid, preferably formic acid, or acid mixture, to provide the compounds of Formula I. The reaction may be performed from about room temperature to about the reflux temperature of the reaction mixture. The resulting compound is isolated by normal extractive workup and may be purified by crystallization or chromatography. Compounds of Formula I where X' is —$SO_2NR^9R^{10}$ and $R^9$ is a nitrogen protecting group are deprotected under standard conditions to provide the secondary sulfonamides of the present invention.

The O-substituted oximes of Formula II are novel and comprise a further embodiment of the present invention.

The process described supra for preparing O-substituted oximes is novel and is an embodiment of the present invention. The process for preparing O-substituted oximes of Formula III:

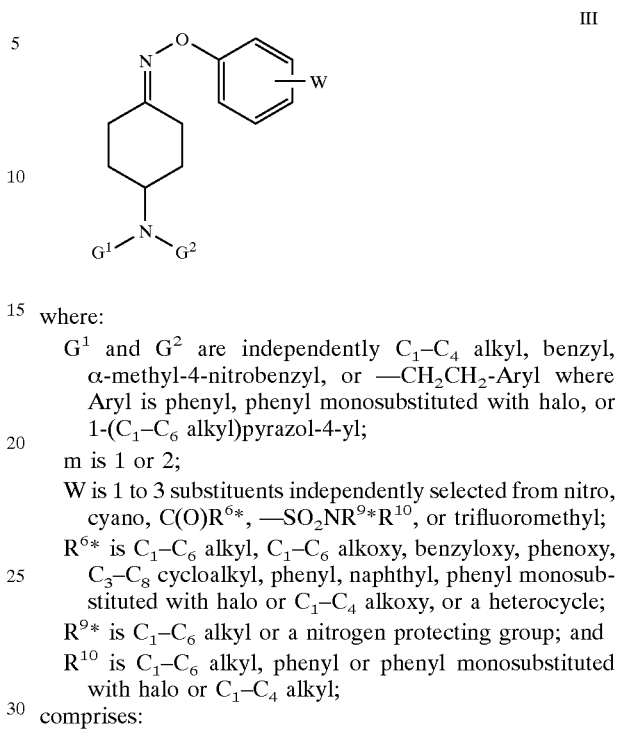

where:
G$^1$ and G$^2$ are independently $C_1$–$C_4$ alkyl, benzyl, α-methyl-4-nitrobenzyl, or —$CH_2CH_2$-Aryl where Aryl is phenyl, phenyl monosubstituted with halo, or 1-($C_1$–$C_6$ alkyl)pyrazol-4-yl;

m is 1 or 2;

W is 1 to 3 substituents independently selected from nitro, cyano, $C(O)R^{6*}$, —$SO_2NR^{9*}R^{10}$, or trifluoromethyl;

$R^{6*}$ is $C_1$–$C_6$ alkyl, $C_1$–$C_6$ alkoxy, benzyloxy, phenoxy, $C_3$–$C_8$ cycloalkyl, phenyl, naphthyl, phenyl monosubstituted with halo or $C_1$–$C_4$ alkoxy, or a heterocycle;

$R^{9*}$ is $C_1$–$C_6$ alkyl or a nitrogen protecting group; and $R^{10}$ is $C_1$–$C_6$ alkyl, phenyl or phenyl monosubstituted with halo or $C_1$–$C_4$ alkyl;

comprises:
a) treating an oxime with a suitable base, optionally in the presence of a crown ether, to prepare the corresponding anion; and
b) treating the anion with an aryl halide of Formula IV:

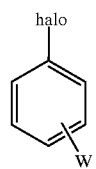

where halo is fluoro, chloro, bromo or iodo and W is as previously defined.

Nitrogen protecting groups useful for these reactions are well known to the skilled artisan (Greene, *Protective Groups in Organic Synthesis*, Second Edition, Wiley Interscience, New York (1991)).

The oxime and base are combined in a suitable aprotic solvent. The oxime need not be totally soluble in the solvent, but must have sufficient solubility to allow the reaction to proceed at an acceptable rate. Suitable solvents include ethers such as tetrahydrofuran, dioxane, tetrahydropyran, and diethyl ether. The preferred reaction solvent is tetrahydrofuran. Bases useful for the process must be capable of deprotonating the oxime and, furthermore, the resulting conjugate acids must not interfere with the reaction. Suitable bases include sodium hydride and potassium hydride, the latter being preferred.

When a crown ether, preferably 18-crown-6, is added to the reaction mixture, it is preferred that from 0.01 to 0.1 equivalents are employed. The deprotonation step may be performed at a temperature from about 0° C. to the reflux temperature of the solvent. It is preferred that the deprotonation step be performed at from about 0° C. to room temperature. It is especially preferred that the deprotonation step be performed at about 0° C. The deprotonation step is usually complete within from about 15 minutes to about 24 hours, but is typically complete within 15 minutes to 1 hour. It is especially preferred that this step be performed in the presence of a crown ether.

The skilled artisan will appreciate that the oxime may be added to a solution or suspension of the base in the reaction solvent, the base may be added to a solution or suspension of the oxime in the reaction solvent, or the oxime and base may be added simultaneously to the reaction solvent. Any of these variations are contemplated by the present invention.

When convenient or desired, all of the reactants may be combined in the same reaction mixture to provide the subject O-substituted oximes. The skilled artisan will appreciate, however, that the ability to perform the process in this manner is limited by the nature of the electron-withdrawing substituents on the aryl halide.

Compounds of Formula I where X is nitro are also useful intermediates for the preparation of other compounds of the invention as illustrated in Synthetic Scheme II. $R^{1*}$, $R^{2*}$, m, $R^3$, and $R^7$ are as previously defined.

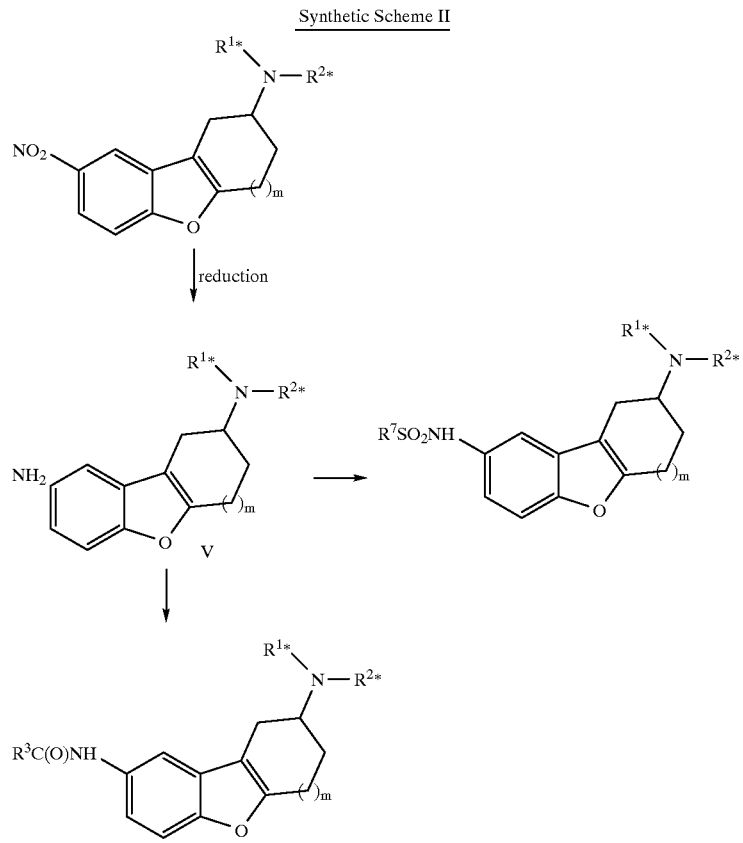

Synthetic Scheme II

The aryl halide may then be added to the reaction mixture containing the oxime anion or, if convenient or desired, the anion mixture may be added to the aryl halide. The resulting mixture is then reacted at from about room temperature to about the reflux temperature of the reaction solvent until the substrates are consumed. The reaction requires from about 15 minutes to about 2 days, but is typically complete within about 1 to 2 hours. The substituted oxime is isolated by normal extractive workup and may be purified by chromatography or crystallization.

The halogen substituent on the aryl halide (IV) may be fluoro, chloro, bromo, or iodo. It is preferred that the halogen substituent be fluoro or chloro, and especially preferred that it be fluoro. The substituent "W" represents from one to three electron-withdrawing substituents. The skilled artisan is well aware of those substituents which are electron withdrawing. Typical classes of electron withdrawing-substituents include nitro, cyano, alkoxycarbonyl, aryloxycarbonyl and trifluoromethyl. Preferred electron-withdrawing substituents include nitro and cyano.

The compounds of Formula I where X is nitro are hydrogenated over a precious metal catalyst, preferably platinum on carbon, and hydrogenated at about ambient temperature at an initial pressure of about 40 p.s.i. for from about 1 to 24 hours in a suitable solvent, such as a lower alkanol or tetrahydrofuran, to give the corresponding amino derivatives of Formula V. The compounds of Formula V are novel and are further embodiments of the present invention.

Compounds where X is $R^3C(O)NH$— or $R^7SO_2NH$— are prepared by reacting the aniline with an appropriate carboxylic acid or sulfonyl chloride, bromide or anhydride, optionally in the presence of an acylation catalyst such as dimethylaminopyridine, in the presence of a suitable base. Suitable bases include amines typically used as acid scavengers, such as pyridine or triethylamine, or commercially available polymer bound bases such as polyvinylpyridine.

Alternatively, compounds where X is $R^3C(O)NH$— are prepared by reacting with an appropriate carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated and purified as described above.

The compounds of Formula V are also useful for the preparation of compounds of the invention where X is hydroxy, cyano, and halo as described in Synthetic Scheme III. $R^{1*}$, $R^{2*}$, and m are as previously described.

solution is then treated with cuprous cyanide and the desired product isolated as previously described.

Compounds where X* is fluoro are prepared by first treating the diazonium salt mixture with fluoroboric acid or, preferably, sodium tetrafluoroborate. The resulting fluoroborate salt precipitates from the reaction mixture. This salt is then filtered, washed with water and dried. The tetrafluoroborate salts of compounds where X* is diazo are novel and are an additional embodiment of the present invention. The dried fluoroborate salt is then heated to provide the corresponding fluoro substituted compound. These fluoroborate salts may also be reacted with dimethylsulfoxide and then hydrolyzed to provide compounds of the invention where X is hydroxy.

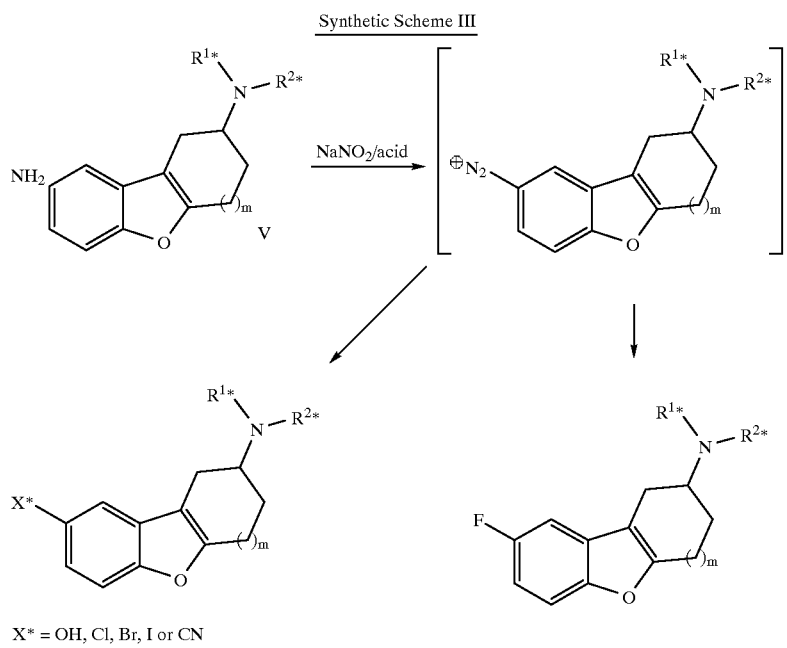

X* = OH, Cl, Br, I or CN

The primary amine of Formula V is added to a minimal amount of a cold, aqueous mineral acid, for example hydrochloric acid, hydrobromic acid, phosphoric acid or sulfuric acid. While it is critical for the amine moieties to be completely protonated by the acid, it is not necessary for all of the corresponding salt to dissolve in the acid, as long as enough is soluble at any given time to allow the reaction to occur. To this mixture is then added a solution of sodium nitrite. The formation of the diazonium salt is rapid. To prepare compounds where X* is chloro or bromo, the diazonium salt mixture is added to a concentrated solution of the corresponding cuprous chloride or bromide in hydrochloric or hydrobromic acid, respectively. Alternatively, the freshly prepared diazonium salt is added to a mixture of metallic copper in hydrochloric or hydrobromic acid. Compounds where X* is iodo may be prepared by adding the diazonium salt directly to a solution of sodium or potassium iodide. Compounds where X* is hydroxy are prepared by adding the diazonium salt directly to a boiling solution of dilute sulfuric acid. The desired products from these transformations may be recovered by normal extractive workup, are may then be purified if necessary or desired by crystallization or chromatography from a suitable solvent.

Compounds where X* is cyano may be prepared by first treating the diazonium salt mixture with a cold, aqueous solution of potassium or sodium carbonate. The resulting The 4-substituted cyclohexanones required for the preparation of compounds of the invention where m is 1 are available by methods well known in the art as illustrated in Synthetic Scheme IV.

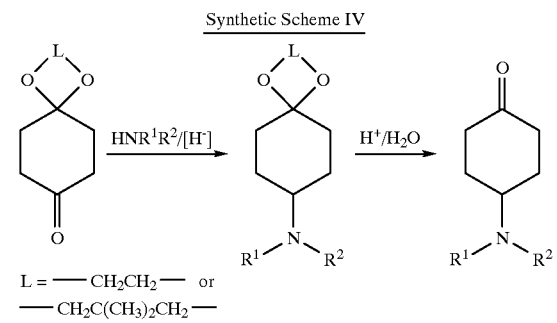

L = —CH$_2$CH$_2$— or
—CH$_2$C(CH$_3$)$_2$CH$_2$—

The 1,4-cyclohexanedione monoketal is reductively aminated with an appropriate amine under standard conditions to give the corresponding 4-aminocyclohexanone ketal. The ketal is then deprotected under either aqueous acid conditions or, preferably, with formic acid to prepare the corresponding 4-aminocyclohexanone.

Compounds of the invention where $R^1=R^2=H$ are prepared from 4-(1-phthalimidyl)cyclohexanone which is available by methods well known in the art, for example, King et al. (*Journal of Medicinal Chemistry*, 36, 1918 (1993)). Briefly, 4-aminocyclohexanol is reacted first with N-carbethoxyphthalimide and the resulting 4-(1-phthalimidyl)cyclohexanol treated with pyridinium chlorochromate to give the desired ketone. The resultant 4-(1-phthalimidyl)cyclohexanone is then reacted as described in Synthetic Scheme I to provide the corresponding 8-substituted-1,2,3,4-tetrahydro-2-(1-phthalimidyl) dibenzofurans of Formula I. The phthalimide is then removed by reaction with hydrazine at any convenient point in the synthetic pathway to provide compounds of the invention where $R^1=R^2=H$.

Compounds of the invention where m=2 are 2-aminocyclohepta[b]benzofurans. These compounds are prepared substantially as described supra. The 4-aminocycloheptanones required for the synthesis of compounds of the present invention where m=2 may be prepared as described in Synthetic Scheme V. $R^{1*}$ and $R^{2*}$ are as previously defined.

Synthetic Scheme V

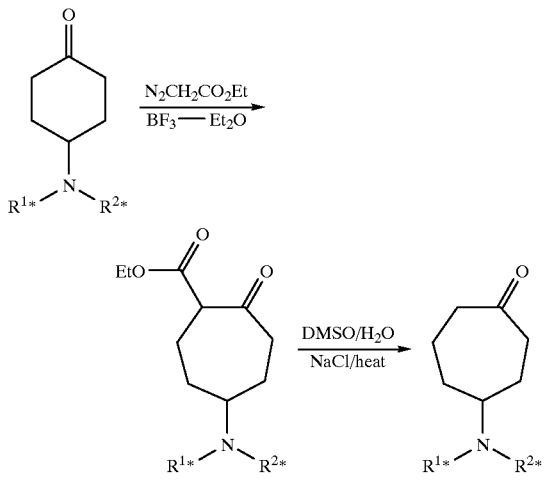

The appropriate 4-aminocyclohexanone in an appropriate solvent, for example diethyl ether, is treated with an appropriate Lewis acid such as boron trifluoride for about 20 minutes to about an hour at room temperature. To this solution is then added ethyl diazoacetate and the resulting mixture is stirred for about 1 hour to about 24 hours at room temperature. The resulting 2-ethoxycarbonyl-5-aminocycloheptanone is isolated by diluting the reaction mixture with aqueous sodium carbonate and extracting with a water immiscible solvent such as diethyl ether. The reaction product is then directly dissolved in dimethylsulfoxide which contains sodium chloride and water. The reaction mixture is heated to about 170° for from about 1 to about 24 hours to effect the decarboxylation. The desired 4-aminocycloheptanone is recovered by diluting the reaction mixture with water and extracting with an appropriate solvent such as diethyl ether. The reaction product may be purified by column chromatography, if desired, prior to further reaction.

After treatment with hydroxylamine, the resulting 4-aminocycloheptanone oxime is subjected to the same reaction scheme as described in Synthetic Scheme I. The asymmetry in the cycloheptanone, however, leads to the production of the following two isomers:

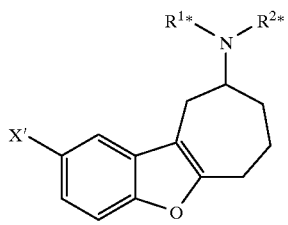

ISOMER A

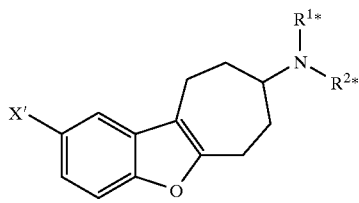

ISOMER B

Isomers A and B may be separated by crystallization or chromatography at any convenient point in the synthesis of the compounds of the invention.

Compounds of the invention where X is bromo are useful intermediates for the introduction of a variety of substituents into the 8-position of the 1,2,3,4-tetra-hydro-2-dibenzofuranamine nucleus and the corresponding 9-position of the 2-aminocyclohepta[b]-benzofuran nucleus. For example, the bromo substituted substrate may be used to provide compounds of the invention where X is —COOH as described in Synthetic Scheme VI. $R^{1}$ and $R^{2}$ are $C_1$–$C_4$ alkyl or benzyl.

Synthetic Scheme VI

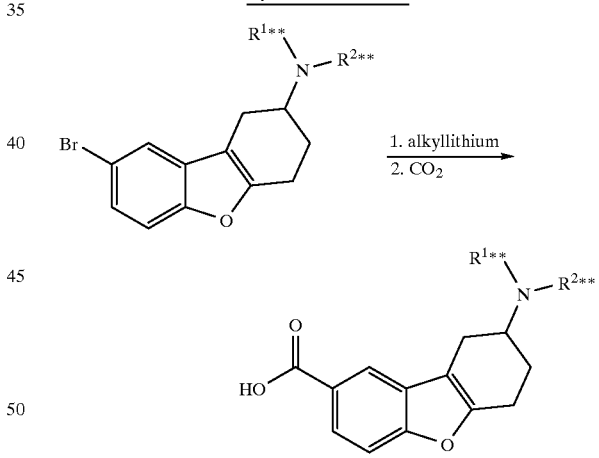

A solution of the bromo compound in an appropriate solvent, such as tetrahydrofuran or diethyl ether, is treated with an alkyllithium, such as n-butyl- or tert-butyllithium, at a temperature of about −70° C. for about an hour to effect a halogen-metal exchange. The solution is then saturated with carbon dioxide to prepare the corresponding carboxylic acid.

Compounds of the invention where $R^6$ is —$NHR^8$ are prepared by reacting the corresponding carboxylic acids with a compound of formula $R^8$—$NH_2$ under the amide coupling conditions previously described. Compounds of Formula I where X is —C(O)OH are novel and are also embodiments of the present invention.

The skilled artisan will appreciate that the carboxylic acids and carboxamides may also be prepared from the corresponding compounds of Formula I where X is cyano. Carboxylic acids are prepared by heating the cyano compound in an aqueous acid. Carboxamides are prepared by heating the cyano compound in a suitable solvent, for example chloroform or xylene, in the presence of polyphosphoric acid.

Compounds of the invention where X is $R^6C(O)$— and $R^1$ and $R^2$ are independently hydrogen are available by subjecting the corresponding 2-dibenzylamino compounds to catalytic hydrogenation conditions over a precious metal catalyst, such as palladium on carbon, or over Raney nickel. These reactions are typically performed in a lower alkanol or tetrahydrofuran at room temperature to about 60° C., for from about 1 hour to 24 hours, at a hydrogen pressure of about 60 p.s.i.

Compounds where either or both of $R^1$ or $R^2$ are hydrogen may be further functionalized to prepare other compounds of the invention by reductive alkylation. Under these conditions the primary or secondary amine is reacted with an appropriate aldehyde or ketone to prepare the corresponding imine or enamine. The imine or enamine is then reduced to the desired compound by catalytic hydrogenation or by reduction with an appropriate hydride reducing reagent in the presence of an acid.

Preferably, the transformation is performed by direct alkylation. The starting primary or secondary amine and a base are combined in the reaction solvent followed by the addition of the alkylating agent. The solvent may be any non-reactive solvent typically used for alkylations of this type such as acetonitrile, dimethylformamide or N-methyl-2-pyrrolidinone, limited by the solubility of the substrates. The base must be sufficiently basic to neutralize the acid generated during the progress of the reaction but not so basic as to deprotonate other sites in the substrate giving rise to other products. Additionally, the base must not compete to any great extent with the substrate for the alkylating agent. Bases typically used for these reactions are sodium carbonate or potassium carbonate. The reaction mixture is typically stirred at room temperature to 80° C., for about 8 hours to 3 days. The alkylated products are isolated by concentration of the reaction mixture under reduced pressure followed by partitioning of the resultant residue between water and a suitable organic solvent such as ethyl acetate, diethyl ether, dichloromethane, ethylene chloride, chloroform or carbon tetrachloride. The isolated product may be purified by chromatography, crystallization from a suitable solvent, salt formation or a combination of these techniques.

The specific alkylating agent employed is determined by its commercial availability or a convenient synthesis from commercially available starting materials. The preferred alkylating agents for synthesis of compounds of this invention are selected from appropriate chlorides, bromides, iodides, or methanesulfonates. Alkylating agents where the leaving group is chloro are prepared from the corresponding alcohol by standard methods, preferably by treating the alcohol with neat thionyl chloride at ambient temperature. Alkylating agents where the leaving group is methanesulfonyloxy are prepared by treating a solution of an appropriate alcohol in a suitable anhydrous solvent such as tetrahydrofuran, diethyl ether, p-dioxane or acetonitrile, which contains a base. The base must be sufficiently basic to neutralize the acid generated during the progress of the reaction but not so basic as to deprotonate other sites in the substrate giving rise to other products. Additionally, the base must not compete to any great extent with the substrate for the sulfonating reagent and must have sufficient solubility in the reaction solvent. Bases typically used in these reactions are tertiary amines such as pyridine, triethylamine or N-methylmorpholine. To the reaction mixture is then added the sulfonating reagent with cooling. The sulfonating reagent may be a methanesulfonyl halide, such as the chloride, or methanesulfonic anhydride. The reaction mixture is allowed to react from 1 hour to 24 hours at ambient temperature. The product is isolated by concentrating the reaction mixture under reduced pressure followed by partitioning the residue between water and an appropriate organic solvent such as dichloromethane, ethylene chloride, chloroform or carbon tetrachloride. The isolated product is used directly in the alkylation step.

The compounds of the present invention possess a chiral center, and as such exist as racemic mixtures or individual enantiomers. As stated above, racemates and the individual enantiomers are all part of the present invention. The individual enantiomers may be resolved by fractional crystallization of salts of the racemic bases and enantiomerically pure acids, for example, ditoluoyltartaric acid. Alternatively, the individual enantiomers may be prepared by the use of a chiral auxiliary during the preparation of the compound as described in the following Synthetic Scheme VII.

Synthetic Scheme VII

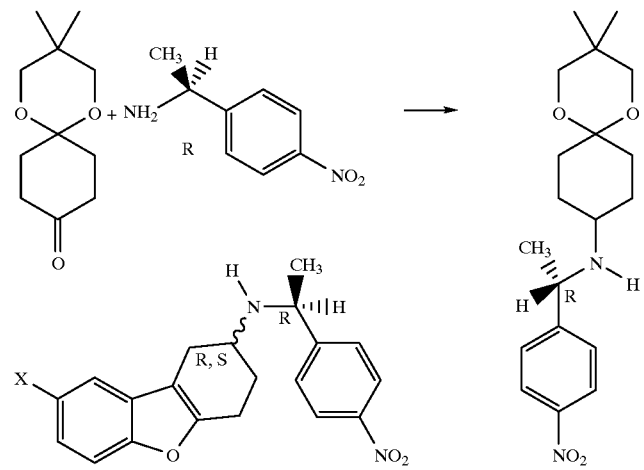

-continued

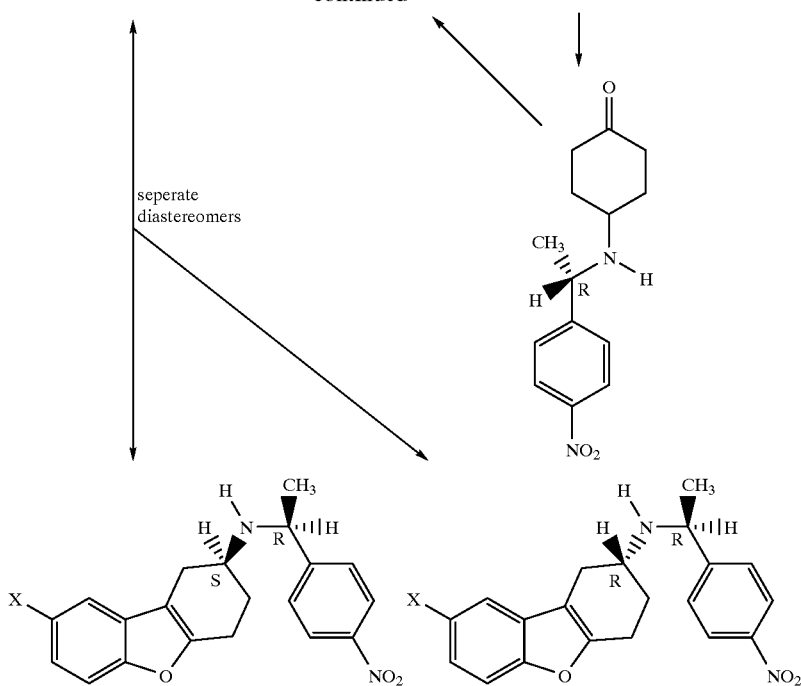

1,4-cyclohexanedione mono-(2,2-dimethylpropane-1,3-diol)ketal is reductively aminated under standard conditions with an enantiomer of α-methyl-(4-nitrophenyl)-ethylamine (Synthetic Scheme VII illustrates the use of the R-(+)-enantiomer). The ketal is removed as described previously and the resulting aminocyclohexanone is subjected to the reaction conditions described for Synthetic Scheme I to give a diastereomeric mixture. The diastereomers are then separated by chromatography or fractional crystallization. The amine may then be treated, if desired, with an appropriate alkylating agent, for example an appropriate alkyl halide, to prepare the corresponding quaternary salt prior to cleavage of the α-methyl-(4-nitrophenyl)ethyl moiety. The skilled artisan will appreciate that while Synthetic Scheme IX illustrates the use of a cyclohexanone to prepare compounds of Formula I where m=1, the synthetic methodology is also applicable for the preparation of those compounds of Formula I where m=2.

Cleavage of the α-methyl-(4-nitrophenyl)ethyl moiety is achieved by reduction of the 4-nitro group followed by acid catalyzed solvolysis of the resulting α-methyl-(4-aminophenyl)ethyl moiety. Reduction of the nitro group can be accomplished by a wide range of reducing agents including, for example, titanium tetrachloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the α-methyl-(4-nitrophenyl)ethyl moiety is hydrogenation of the amine monohydrochloride in methanol over a platinum catalyst.

The skilled artisan will also appreciate that the order in which the steps are performed to prepare the compounds of the present invention are not important in many cases. The following Preparations and Examples will serve to illustrate some of the variations possible within the synthetic pathways described.

Preparation I

4-Dimethylaminocyclohexanone
4-Dimethylaminocyclohexanone (2,2-dimethylpropane-1,3-diol)ketal To a solution of 25.0 gm (0.55 Mol) of dimethylamine in 500 mL methanol were added 50.0 gm (0.25 Mol) of 1,4-cyclohexanedione mono-2,2-dimethylpropane-1,3-diol ketal and the reaction mixture was allowed to stir for 2 hours at room temperature. To this solution were then gradually added 31.69 gm (0.50 Mol) of sodium cyanoborohydride. Once this addition was complete, acetic acid was added to adjust the mixture to a pH of about 6. The pH was monitored periodically and acetic acid additions continued to maintain the pH at about 6. When the addition of acetic acid no longer resulted in gas evolution, the reaction mixture was allowed to stir at room temperature for 18 hours. The reaction mixture was then concentrated under reduced pressure to a volume of about 100 mL and was then partitioned between 1N sodium hydroxide and dichloromethane. The remaining aqueous phase was treated with saturated aqueous sodium chloride and was again extracted with dichloromethane. These organic phases were combined, dried over sodium sulfate and concentrated under reduced pressure to give 40.15 gm (70%) of the desired compound as a yellow oil.

MS(m/e) 228(M+1)

Removal of Ketal

A solution of 18.4 gm (81 mMol) of 4-dimethylaminocyclohexanone (2,2-dimethylpropane-1,3-diol)ketal in 250 mL of 90% formic acid was heated at reflux for 3 hours. The reaction mixture was then stirred at room temperature for 3 days. The reaction mixture was then diluted with 250 mL water and was concentrated to a volume of about 250 mL on a rotary evaporator. The dilution/concentra-tion sequence was then repeated two more times. The residue was then further concentrated to a volume of about 50 mL, made basic with 5 N sodium hydroxide and extracted with dichloromethane. The organic phases were combined, dried over sodium sulfate and concentrated under reduced pressure to give 11.8 gm (100%) of the desired compound as a yellow oil.

MS(m/e): 141 (M$^+$) NMR(CDCl$_3$): δ2.50 (m, 2H), 2.28 (m, 2H), 2.28 (m, 6H), 2.01 (m, 2H), 1.80 (m, 2H).

Preparation II 4-(1-Phthalimidyl)cycloheptanone

To a stirred solution of 5.00 gm (20.6 mMol) of 4-(1-phthalimidyl)cyclohexanone in 30 mL of diethyl ether were added 3.79 mL (30.8 mMol) of boron trifluoride ethereate. After stirring for 20 minutes at room temperature, 3.24 mL (30.8 mMol) ethyl diazoacetate were added dropwise. The resultant solution was stirred for 16 hours at room temperature. The reaction mixture was diluted with saturated aqueous sodium carbonate and was then extracted with diethyl ether. The combined organic extracts were dried over sodium sulfate and concentrated under reduced pressure. The residue was dissolved in 15 mL of dimethylsulfoxide. To this solution were added 1.3 mL of water and 1.5 gm of sodium chloride. The resulting mixture was heated at 170° C. for 7 hours. The reaction mixture was then cooled, poured into 150 mL of water and extracted with diethyl ether. The combined organic phases were washed sequentially with water and saturated aqueous sodium chloride, dried over sodium sulfate and concentrated under reduced pressure. The residue was subjected to silica gel chromatography, eluting with (6:4) hexane/ethyl acetate. Fractions shown to contain product were combined and concentrated under reduced pressure to give 4.17 gm (79%) of the title compound. MS(m/e): 257(M$^+$)

Preparation III

4-Dimethylaminocyclohexanone oxime

A mixture of 1.78 gm (10 mMol) of 4-dimethylaminocyclohexanone hydrochloride and 0.70 gm (10 mMol) of hydroxylamine hydrochloride in 25 mL ethanol was treated with 3 mL pyridine and then heated at reflux for 30 minutes. The reaction mixture was then cooled to room temperature and stored at 4° C. for 18 hours. The resulting crystalline solid was collected and washed with cold ethanol. The solid was then dissolved in water and the aqueous solution made basic by the addition of potassium carbonate. The aqueous phase was then extracted with dichloromethane which contained a small amount of isopropanol. The organic extracts were combined, dried over sodium sulfate and concentrated under reduced pressure to provide a crystalline solid. This solid was recrystallized from ethanol to provide 1.05 gm (67%) of the desired oxime.

m.p.=96–7° C. MS(m/e): 156(M$^+$) Calculated for $C_8H_{16}N_2O$: Theory: C, 61.51; H, 10.32; N, 17.93. Found: C, 61.23; H, 10.44; N, 17.81.

EXAMPLE 1

N,N-Dimethyl-8-amino-1,2,3,4-tetrahydro-2-dibenzofuranamine dihydrochloride hemihydrate O-(4-Fluoronitrophenyl)-4-dimethylaminocyclohexanone oxime To a suspension of 1.50 gm (13.1 mMol) of potassium hydride (35% in mineral oil) in 80 mL of tetrahydrofuran was added 2.00 gm (12.8 mMol) of 4-dimethylaminocyclohexane oxime in portions with cooling. After stirring the reaction mixture for about 20 minutes, a solution of 2.00 gm (14.2 mMol) of 4-fluoronitrobenzene in tetra-hydrofuran was added followed by 50 mg of 18-crown-6 ether. After stirring for 2 hours the reaction mixture was quenched by pouring into cold water. The resulting mixture was extracted with dichloromethane. The combined organic extracts were washed with cold aqueous sodium hydroxide (0.1 M) followed by saturated aqueous sodium chloride. The remaining organic solution was dried over sodium sulfate and concentrated under reduced pressure to provide 4.52 gm of crude product.

A portion (3.52 gm) of this material was subjected to silica gel chromatography eluting with 5% methanol (containing about 5% ammonium hydroxide) in chloroform. Fractions containing product were combined and concentrated under reduced pressure to provide 2.64 gm of the desired compound.

m.p.=74–5° C. MS(m/e): 277(M$^+$) Calculated for $C_{14}H_{19}N_3O_3$: Theory: C, 60.63; H, 6.91; N, 15.15. Found: C, 60.88; H, 6.99; N, 15.31.

N,N-Dimethyl-8-nitro-1,2,3,4-tetrahydro-2-dibenzofuranamine

A solution of 2.50 gm (9.03 mMol) of O-(4-fluoronitrophenyl)-4-dimethylaminocyclohexanone oxime in 25 mL of 96% formic acid was heated slowly to reflux under a nitrogen atmosphere. After 90 minutes the reaction mixture was cooled to room temperature and most of the formic acid removed under reduced pressure. The residue was dissolved in water and the aqueous phase made basic by addition of 2N sodium hydroxide. The aqueous mixture was then extracted with dichloromethane containing a small amount of isopropanol. The combined extracts were combined and concentrated under reduced pressure to provide 1.2 gm of a crystalline solid. This solid was subjected to silica gel chromatography, eluting with a gradient of chloroform containing from 2–5% methanol (containing about 5% ammonium hydroxide). Fractions containing product were combined and concentrated under reduced pressure. The solid residue was recrystallized from hexane to provide 0.91 gm (39%) of the desired compound.

m.p.=88–89° C. MS(m/e): 260(M$^+$) Calculated for $C_{14}H_{16}N_2O_3$: Theory: C, 64.60; H, 6.20; N, 10.76. Found: C, 64.41; H, 6.36; N, 10.47.

Reduction of Nitro Group

A solution of 0.38 gm (1.46 mMol) of N,N-dimethyl-8-nitro-1,2,3,4-tetrahydro-2-dibenzofuranamine in 150 mL of ethanol was hydrogenated over 200 mg of 5% platinum on carbon at 40 p.s.i. for 2 hours at room temperature. The catalyst was removed by filtration and the filtrate concentrated under reduced pressure. The residue was subjected to radial chromatography (silica gel, 2 mm), eluting with 10% methanol (containing about 5% ammonium hydroxide) in chloroform. Fractions containing product were combined and concentrated under reduced pressure to provide 265 mg of N,N-dimethyl-8-amino-1,2,3,4-tetrahydro-2-dibenzofuranamine as a viscous oil. The oil was dissolved in diethyl ether and this solution treated with hydrogen chloride. The precipitated salt was filtered and dried to provide 337 mg (74%) of the title compound.

MS(m/e): 230(M$^+$) Calculated for $C_{14}H_{18}N_2O\cdot2HCl$: Theory: C, 55.45; H, 6.65; N, 9.24. Found: C, 55.12; H, 6.58; N, 9.00.

EXAMPLE 2

N-(N,N-Dimethyl-1,2,3,4-tetrahydro-2-aminodibenzofur-8-yl)methanesulfonamide

A mixture of 9.0 mg (0.029 mMol) of N,N-dimethyl-8-amino-1,2,3,4-tetrahydro-2-dibenzofuranamine dihydrochloride hemihydrate and 29.0 mg (0.115 mMol) polyvinylpiperidine in 1.0 mL dichloromethane was heated to 60° C. for 45 minutes. To this homogeneous mixture were added 1 mg (0.036 mMol) of methanesulfonyl chloride. The reaction mixture was agitated for 2 days at ambient temperature. To this mixture were then added 58.0 mg (0.058 mMol) aminomethylated polystyrene and the reaction agitated for an additional 18 hours. The reaction mixture was then filtered and the volatiles evaporated to provide 5.7 mg (64%) of the title compound.

MS(m/e): 309(M+1)

EXAMPLE 3

N-(N,N-Dimethyl-1,2,3,4-tetrahydro-2-aminodibenzofur-8-yl)-4-fluorobenzenesulfonamide Beginning with 9.0 mg (0.029 mMol) of N,N-dimethyl-8-amino-1,2,3,4-tetrahydro-2-dibenzofuranamine dihydrochloride hemihydrate and 7.0 mg (0.036 mMol) of 4-fluorobenzenesulfonyl chloride, 5.61 mg (50%) of the title compound were recovered by the procedure described in Example 2.

MS(m/e): 389(M+1)

EXAMPLE 4

N-(N,N-Dimethyl-1,2,3,4-tetrahydro-2-aminodibenzofur-8-yl)acetamide

Beginning with 9.0 mg (0.029 mMol) of N,N-dimethyl-8-amino-1,2,3,4-tetrahydro-2-dibenzofuranamine dihydrochloride hemihydrate and 2.8 mg (0.036 mMol) of acetyl chloride, 6.05 mg (77%) of the title compound were recovered by the procedure described in Example 2.

MS(m/e): 273(M+1)

EXAMPLE 5

N-(N,N-Dimethyl-1,2,3,4-tetrahydro-2-aminodibenzofur-8-yl)cyclopropanamide

Beginning with 9.0 mg (0.029 mMol) of N,N-dimethyl-8-amino-1,2,3,4-tetrahydro-2-dibenzofuranamine dihydrochloride hemihydrate and 4.3 mg (0.036 mMol) of cyclopropanecarbonyl chloride, the title compound was recovered by the procedure described in Example 2.

MS(m/e): 299(M+1)

EXAMPLE 6

N-(N,N-Dimethyl-1,2,3,4-tetrahydro-2-aminodibenzofur-8-yl)cyclobutanamide

Beginning with 9.0 mg (0.029 mMol) of N,N-dimethyl-8-amino-1,2,3,4-tetrahydro-2-dibenzofuranamine dihydrochloride hemihydrate and 4.3 mg (0.036 mMol) of cyclobutanecarbonyl chloride, 6.7 mg (74%) of the title compound were recovered by the procedure described in Example 2.

MS(m/e): 313(M+1)

EXAMPLE 7

N-(N,N-Dimethyl-1,2,3,4-tetrahydro-2-aminodibenzofur-8-yl)benzamide

Beginning with 9.0 mg (0.029 mMol) of N,N-dimethyl-8-amino-1,2,3,4-tetrahydro-2-dibenzofuranamine dihydrochloride hemihydrate and 5.06 mg (0.036 mMol) of benzoyl chloride, 7.02 mg (52%) of the title compound were recovered by the procedure described in Example 2.

MS(m/e): 334(M+1)

EXAMPLE 8

N-(N,N-Dimethyl-1,2,3,4-tetrahydro-2-aminodibenzofur-8-yl)-2-chlorobenzamide

Beginning with 9.0 mg (0.029 mMol) of N,N-dimethyl-8-amino-1,2,3,4-tetrahydro-2-dibenzofuranamine dihydrochloride hemihydrate and 5.8 mg (0.036 mMol) of 2-chlorobenzoyl chloride, 6.6 mg (64%) of the title compound were recovered by the procedure described in Example 2.

MS(m/e): 355(M+1)

EXAMPLE 9

N-(N,N-Dimethyl-1,2,3,4-tetrahydro-2-aminodibenzofur-8-yl)-2,4-difluorobenzamide Beginning with 9.0 mg (0.029 mMol) N,N-dimethyl-8-amino-1,2,3,4-tetrahydro-2-dibenzofuranamine dihydrochloride hemihydrate and 6.3 mg (0.036 mMol) of 2,4-difluorobenzoyl chloride, 6.91 mg (64%) of the title compound were recovered by the procedure described in Example 2.

MS(m/e) 371(M+1)

EXAMPLE 10

N-(N,N-Dimethyl-1,2,3,4-tetrahydro-2-aminodibenzofur-8-yl)-2-trifluoromethyl-4-fluorobenzamide Beginning with 9.0 mg (0.029 mMol) of N,N-dimethyl-8-amino-1,2,3,4-tetrahydro-2-dibenzofuranamine dihydrochloride hemihydrate and 8.1 mg (0.036 mMol) of 2-trifluoromethyl-4-fluorobenzoyl chloride, 10.5 mg (86%) of the title compound were recovered by the procedure described in Example 2.

MS(m/e): 421(M+1)

EXAMPLE 11

N-(N,N-Dimethyl-1,2,3,4-tetrahydro-2-aminodibenzofur-8-yl)-2-thiophenecarboxamide Beginning with 9.0 mg (0.029 mMol) of N,N-dimethyl-8-amino-1,2,3,4-tetrahydro-2-dibenzofuranamine dihydrochloride hemihydrate and 5.3 mg (0.036 mMol) of 2-thiophenecarbonyl chloride, 8.0 mg (81%) of the title compound were recovered by the procedure described in Example 2.

MS(m/e): 341(M+1)

General Procedure for the Coupling of Carboxylic Acids with N,N-dimethyl-8-amino-1,2,3,4-tetrahydro-2-dibenzofuranamine A suspension of 1 equivalent of N,N-dimethyl-8-amino-1,2,3,4-tetrahydro-2-dibenzofuranamine dihydrochloride hemihydrate and 4–5 equivalents of polyvinylpiperidine in 1 mL chloroform is heated at 60° C. for 45 minutes. To this mixture are then added 4–5 equivalents of polymer bound 1-ethyl-3-(3-dimethylamino-propyl)carbodiimide (Desai, et al., *Tetrahedron Letters*, 34(48), 7685 (1993)) and 2–3 equivalents of the carboxylic acid. The reaction is agitated at 70° C. until the reaction is complete. An isocyanate resin may be added to remove unreacted starting material if required. The resins are removed by filtration and the product is isolated by evaporation of solvent. This procedure is illustrated by Examples 12-16.

EXAMPLE 12

N-(N,N-Dimethyl-1,2,3,4-tetrahydro-2-aminodibenzofur-8-yl)-3-thiophenecarboxamide Beginning with 9.0 mg (0.029 mMol) of N,N-dimethyl-8-amino-1,2,3,4-tetrahydro-2-dibenzofuranamine dihydrochloride hemihydrate and 7.4 mg (0.058 mMol) of 3-thiophenecarboxylic acid, 1.3 mg (13%) of the title compound were recovered.

MS(m/e): 341(M+1)

EXAMPLE 13

N-(N,N-Dimethyl-1,2,3,4-tetrahydro-2-aminodibenzofur-8-yl)-2-furamide

Beginning with 9.0 mg (0.029 mMol) of N,N-dimethyl-8-amino-1,2,3,4-tetrahydro-2-dibenzofuranamine dihydrochloride hemihydrate and 6.5 mg (0.058 mMol) of 2-furoic acid, 0.8 mg (8.5%) of the title compound were produced.

MS(m/e): 325(M+1)

EXAMPLE 14

N-(N,N-Dimethyl-1,2,3,4-tetrahydro-2-aminodibenzofur-8-yl)-3-furamide

Beginning with 9.0 mg (0.029 mMol) N,N-dimethyl-8-amino-1,2,3,4-tetrahydro-2-dibenzofuranamine dihydrochloride hemihydrate and 6.5 mg (0.058 mMol) of 3-furoic acid, 0.9 mg (9.6%) of the title compound were produced.

MS(m/e): 325(M+1)

EXAMPLE 15

N-(N,N-Dimethyl-1,2,3,4-tetrahydro-2-aminodibenzofur-8-yl)-5-chloro-2-furamide

Beginning with 9.0 mg (0.029 mMol) of N,N-dimethyl-8-amino-1,2,3,4-tetrahydro-2-dibenzofuranamine dihydrochloride hemihydrate and 8.5 mg (0.058 mMol) of 5-chloro-2-furoic acid, 0.8 mg (7.7%) of the title compound were produced.

MS(m/e): 359(M+1)

EXAMPLE 16

N-(N,N-Dimethyl-1,2,3,4-tetrahydro-2-aminodibenzofur-8-yl)-2-methyl-3-furamide

Beginning with 9.0 mg (0.029 mMol) of N,N-dimethyl-8-amino-1,2,3,4-tetrahydro-2-dibenzofuranamine dihydrochloride hemihydrate and 7.3 mg (0.058 mMol) of 2-methyl-3-furoic acid, 1.5 mg (15%) of the title compound were produced.

MS(m/e): 339(M+1)

EXAMPLE 17

N-(N,N-Dimethyl-1,2,3,4-tetrahydro-2-aminodibenzofur-8-yl)-4-fluorobenzamide

To a solution of 0.132 gm (0.57 mMol) of N,N-dimethyl-8-amino-1,2,3,4-tetrahydro-2-dibenzofuranamine in 5 mL of tetrahydrofuran were added 1.5 mL of triethylamine followed by 0.10 mL (0.13 gm, 0.85 mMol) of 4-fluorobenzoyl chloride. The resulting mixture was stirred at room temperature for 90 minutes at which time the reaction mixture was diluted with 0.1 N aqueous sodium hydroxide. This aqueous solution was extracted with dichloromethane and the organic phases were washed sequentially with water and saturated aqueous sodium chloride. The dichloromethane solution was dried over sodium sulfate and concentrated under reduced pressure. This residue was dissolved in dilute aqueous tartaric acid and then washed with dichloromethane. The aqueous phase made basic with aqueous sodium carbonate and was then extracted with dichloromethane. These dichloro-methane extracts were combined and concentrated under reduced pressure. The residue was subjected to radial chromatography (silica gel, 2 mm), eluting with 5% methanol (containing 5% ammonium hydroxide) in chloro-form. Fractions containing product were combined and concentrated under reduced pressure. The residue was crystallized from toluene/hexane to provide 0.130 gm (64%) of the title compound in two crops.

m.p.=167–8° C. MS(m/e): 352(M$^+$) Calculated for $C_{21}H_{21}N_2OF$: Theory: C, 71.57; H, 6.01; N, 7.95. Found: C, 71.84; H, 6.11; N, 7.95.

EXAMPLE 18

N-(N,N-Dimethyl-1,2,3,4-tetrahydro-2-aminodibenzofur-8-yl)-pyridine-4-carboxamide Beginning with 0.132 gm (0.57 mMol) of N,N-dimethyl-8-amino-1,2,3,4-tetrahydro-2-dibenzofuranamine and 0.15 gm (0.84 mMol) of isonicotinoyl chloride, 0.081 gm (42%) of the title compound were obtained by the procedure described in Example 20.

m.p.=146–7° C. MS(m/e): 335(M$^+$) Calculated for $C_{20}H_{20}N_3O_2$: Theory: C, 71.62; H, 6.31; N, 12.53. Found: C, 71.77; H, 6.48; N, 12.36.

EXAMPLE 19

(2R)- and (2S)- N-((R)-(+)-α-(4-Nitrophenyl)ethyl)-8-nitro-1,2,3,4-tetrahydro-2-dibenzofuranamine Reductive Alkylation To a solution of 20.0 gm (101 mMol) 1,4-cyclohexanedione (2,2-dimethyl)propane-1,3-diol monoketal in 250 mL of methanol were added 35.0 gm (173 mMol) of R-(+)-α-(4-nitrophenyl)ethylamine hydrochloride, 25.0 gm (398 mMol) of sodium cyanoborohydride and 10 mL of acetic acid. The reaction mixture was stirred for 18 hours at room temperature. To the reaction mixture was then added an additional charge of 25.0 gm (398 mMol) of sodium cyanoborohydride and the reaction mixture was stirred for an additional 18 hours at room temperature. The reaction mixture was then treated with dilute aqueous tartaric acid and the solution exhaustively extracted with dichloromethane. The remaining aqueous phase was made basic with aqueous sodium hydroxide and extracted with dichloromethane. These dichloromethane extracts were combined, dried over sodium sulfate and concentrated under reduced pressure to give 33.7 gm (96%) of N-((R)-(+)-α-(4-nitrophenyl)ethyl)-4-aminocyclohexanone 2,2-dimethylpropane-1,2-diol ketal as a brownish yellow oil.

MS(m/e): 348(M$^+$)

Removal of Ketal

A solution of 33.42 gm (95.9 mMol) of N-((R)-(+)-α-(4-nitrophenyl)ethyl)-4-aminocyclohexanone 2,2-dimethylpropane-1,2-diol ketal in 250 mL of 98% formic acid was heated to 40° C. for 66 hours. The reaction mixture was concentrated under reduced pressure to a volume of about 50 mL and was then basified with aqueous potassium carbonate. This mixture was extracted with dichloromethane and the organic extract was then dried over sodium sulfate and concentrated under reduced pressure to give 22.36 gm (89%) N-((R)-(+)-α-(4-nitrophenyl)ethyl)-4-aminocyclohexanone as a brown oil.

Preparation of Oxime

A mixture of 5.24 gm (20 mMol) of N-((R)-(+)-α-(4-nitrophenyl)ethyl)-4-aminocyclohexanone and 1.40 gm (20 mMol) of hydroxylamine hydrochloride in 40 mL of ethanol was heated to reflux on a steam bath for 30 minutes. The reaction mixture was cooled for 18 hours at 4° C. after which N-((R)-(+)-α-(4-nitrophenyl)ethyl)-4-aminocyclo-hexanone oxime hydrochloride was isolated by filtration. When dried under reduced pressure, 3.95 gm (63%) of the desired oxime hydrochloride was recovered.

m.p.=238–9° C. (dec.) MS(m/e): 277($M^+$) Calculated for $C_{14}H_{19}N_3O_3$·HCl: Theory: C, 53.59; H, 6.42; N, 13.39. Found: C, 53.63; H, 6.58; N, 13.07. $[α]_D$(c=1.0, methanol): +61°

Alkylation of Oxime

N-((R)-(+)-α-(4-nitrophenyl)ethyl)-4-aminocyclohexanone oxime was prepared by partitioning 3.80 gm (12.1 mMol) of the corresponding hydrochloride salt between dilute aqueous sodium bicarbonate and dichloromethane. After the phases were separated the organic phase was dried over sodium sulfate and then concentrated under reduced pressure to provide the desired free base as a viscous oil.

The free base was dissolved in 100 mL of tetrahydrofuran and to this solution were added 3.00 gm (21.3 mMol) of 4-fluoronitrobenzene and 0.30 gm of 18-crown-6 ether. The resulting solution was maintained at about 0° C. as 1.30 gm (11.4 mMol) of potassium hydride (35% in mineral oil) were added dropwise over 20 minutes. The reaction mixture was stirred for 2 hours and was then quenched by the addition of cold water followed by extraction with dichloromethane. The organic phases were combined, washed with saturated aqueous sodium chloride, dried over sodium sulfate and concentrated under reduced pressure to provide a crystalline residue. The residue was subjected to silica gel chromatography, eluting with a gradient system of chloroform and 0–2% methanol (containing 5% ammonium hydroxide). Fractions containing product were combined and concentrated under reduced pressure to provide 4.30 gm (95%) of the desired compound as yellow crystals. This material was recrystallized from toluene/hexane to provide 3.88 gm (85%) N-((R)-α-(4-nitrophenyl)ethyl)-4-aminocyclohexanone 4-nitrophenyl-oxime.

m.p.=96–7° C. MS(m/e): 398($M^+$) Calculated for $C_{20}H_{22}N_4O_5$: Theory: C, 60.29; H, 5.57; N, 14.06. Found: C, 60.33; H, 5.68; N, 13.95. $[α]_D$(c=1.0, methanol): +64°

Cyclization

A solution of 3.75 gm (9.41 mMol) N-((R)-α-(4-nitrophenyl)ethyl)-4-aminocyclohexanone 4-nitrophenyl-oxime in 40 mL of formic acid was stirred at reflux for 2 hours. The reaction mixture was cooled to room temperature and was then poured into cold water. The solution was carefully made basic to pH~10 by the gradual addition of about 400 mL of cold 2N sodium hydroxide followed by aqueous sodium carbonate. The aqueous mixture was then extracted with dichloromethane. The extract was washed with aqueous sodium carbonate, dried over sodium sulfate and concentrated under reduced pressure. The residue was subjected to silica gel chromatography, eluting with ethyl acetate.

First Eluting N-((R)-α-(4-nitrophenyl)ethyl)-8-nitro-1,2,3,4-tetrahydro-2-dibenzofuranamine diastereomer The faster eluting diastereomer was recovered as 0.82 gm (23%) of a crystalline solid after recrystallization from toluene/hexane.

m.p.=170–1° C. MS(m/e): 381($M^+$) Calculated for $C_{20}H_{19}N_3O_5$: Theory: C, 62.99; H, 5.02; N, 11.02. Found: C, 62.99; H, 5.03; N, 10.78.

Last Eluting N-((R)-α-(4-nitrophenyl)ethyl)-8-nitro-1,2,3,4-tetrahydro-2-dibenzofuranamine diastereomer The slower eluting diastereomer was recovered as 0.88 gm (25%) of a crystalline solid after recrystallization from toluene/hexane.

m.p.=164.5–166° C. MS(m/e) : 381($M^+$) Calculated for $C_{20}H_{19}N_3O_5$: Theory: C, 62.99; H, 5.02; N, 11.02. Found: C, 63.27; H, 5.22; N, 11.21.

EXAMPLE 20

(+)-N,N-Dimethyl-8-(tert-butoxycarbonyl)amino-1,2,3,4-tetrahydro-2-dibenzofuranamine Quaternization To a solution of 0.85 gm (2.13 mMol) of the slower eluting diastereomer of N-((R)-α-(4-nitrophenyl)ethyl)-8-nitro-1,2,3,4-tetrahydro-2-dibenzofuranamine in 10 mL acetonitrile were added 2.0 mL of iodomethane followed by 1.0 gm of potassium carbonate. The mixture was stirred for 18 hours at 60° C. and then an additional 1.0 mL iodomethane was added and heating continued for another 18 hours. The reaction mixture was then cooled to room temperature and concentrated under reduced pressure. The residue was heated briefly in 30 ml methanol and, after cooling, was collected on a filter. The methanol washings were combined and concentrated under reduced pressure. Washing the residue with water afforded a small amount of additional product. The solids were combined, washed with cold water and dried to provide 1.00 gm (88%) of (+)-N,N-dimethyl-N-((R)-α-(4-nitrophenyl)ethyl)-8-nitro-1,2,3,4-tetrahydro-2-dibenzofuranammonium iodide.

Calculated for $C_{22}H_{24}N_3O_5I$: Theory: C, 49.17; H, 4.50; N, 7.82; I, 23.62. Found: C, 48.89; H, 4.44; N, 7.65; I, 23.38.

Hydrogenolysis/Hydrogenation

A mixture of 0.95 gm (1.71 mMol) of (+)-N,N-dimethyl-N-((R)-(+)-α-(4-nitrophenyl)ethyl)-8-nitro-1,2,3,4-tetrahydro-2-dibenzofuranammonium iodide and 0.25 gm of 5% platinum on carbon in 250 mL methanol were hydrogenated at room temperature for 6 hours at an initial hydrogen pressure of 40 p.s.i. The reaction mixture was then filtered and warmed to effect methanolysis. The reaction mixture was concentrated under reduced pressure without heat and the residue triturated with diethyl ether to give about 0.800 gm of (+)-N,N-dimethyl-8-amino-1,2,3,4-tetrahydro-2 -dibenzofuranamine hydroiodide as a finely divided, granular solid.

Acylation

The amine hydroiodide was partitioned between dichloromethane and 1N sodium hydroxide. The organic phase was washed with saturated aqueous sodium chloride, dried over sodium sulfate, and then concentrated under reduced pressure to a volume of about 50 mL. To this solution was then added 0.5 gm of di-tert-butyl dicarbonate and the resulting mixture was allowed to stand for 18 hours at room temperature. At this time an additional 0.2 gm of di-tert-butyl dicarbonate were added and the reaction continued for another 18 hours. The reaction mixture was then stirred with aqueous sodium carbonate for 2 days. The organic phase was separated, dried over sodium sulfate and concentrated under reduced pressure. The residue was subjected to silica gel chromatography, eluting with 5% methanol (containing 5% ammonium hydroxide) in chloroform. Fractions containing product were combined and concentrated under reduced pressure to provide 0.224 gm (40%) of the title compound.

MS(m/e): 330(M$^+$) Calculated for $C_{19}H_{26}N_2O_3$: Theory: C, 69.07; H, 7.93; N, 8.48. Found: C, 69.34; H, 7.86; N, 8.29. [α]$_D$(c=1.0, methanol): +62°

EXAMPLE 21

(+)-N-(N,N-Dimethyl-1,2,3,4-tetrahydro-2-aminodibenzofur-8-yl)-4-fluorobenzamide A mixture of 0.090 gm (0.273 mMol) of (+)-N,N-dimethyl-8-(tert-butoxycarbonyl)amino-1,2,3,4-tetrahydro-2-dibenzofuranamine and 1 mL of trifluoro-acetic acid was stirred at room temperature for 20 minutes. The excess trifluoroacetic acid was then removed under reduced pressure. The residue was dissolved in 5 mL of tetrahydrofuran and to this solution were added 1.5 mL of triethylamine followed by 0.05 mL (0.42 mMol) of 4-fluorobenzoyl chloride. After stirring for 1 hour the volatiles were removed under reduced pressure. The residue was taken up in 5 mL of dichloromethane and stirred with dilute aqueous sodium carbonate. After stirring for 16 hours the dichloromethane layer was separated and the aqueous layer extracted with fresh dichloromethane. The dichloromethane extracts were combined, dried over sodium sulfate and concentrated under reduced pressure. The residue was subjected to silica gel chromatography, eluting with 5% methanol (containing 5% ammonium hydroxide) in chloroform. Fractions containing product were combined and concentrated under reduced pressure. The resulting residue was crystallized from toluene/hexane to provide 0.058 gm (60%) of the title compound as a crystalline solid in two crops.

m.p.=137–8° C. Calculated for $C_{21}H_{21}N_2O_2F$: Theory: C, 71.57; H, 6.01; N, 7.95; F, 5.39. Found: C, 71.36; H, 5.86; N, 7.72; F, 5.25. [α]$_D$(c=1.0, methanol): +66°

EXAMPLE 22

(+)-N-(N,N-Dimethyl-1,2,3,4-tetrahydro-2-aminodibenzofur-8-yl)pyridine-4-carboxamide Beginning with 0.100 gm (0.30 mMol) of (+)-N,N-dimethyl-8-(tert-butoxycarbonyl)amino-1,2,3,4-tetrahydro-2-dibenzofuranamine and 0.100 gm (0.56 mMol) of isonicotinoyl chloride hydrochloride, 0.036 gm (36%) of the title compound were recovered in two crops from toluene/hexane by the procedure described in Example 24.

m.p.=146–7° C. Calculated for $C_{20}H_{21}N_3O_2$: Theory: C, 71.62; H, 6.31; N, 12.53. Found: C, 71.37; H, 6.28; N, 12.51. [α]$_D$(c=1.0, methanol): +70.7°

EXAMPLE 23

N,N-Dimethyl-8-cyano-1,2,3,4-tetrahydro-2-dibenzofuranamine

O-(4-cyanophenyl)-4-dimethylcyclohexanone oxime

Beginning with 3.0 gm (19.2 mMol) 4-dimethylaminocyclohexanone oxime and 2.77 gm (22.9 mMol) 4-fluorobenzonitrile, 3.51 gm (71%) of the desired oxime ether were recovered as a dark brown solid by the procedure described in Example 1.

Cyclization

Beginning with 11.69 mMol of the oxime ether and 100 mL formic acid, 1.03 gm (37%) of the title compound were recovered as a tan solid by the procedure described in Example 1.

MS(m/e): 240(M$^+$)

EXAMPLE 24

N,N-Dimethyl-8-carboxamido-1,2,3,4-tetrahydro-2-dibenzofuranamine

A mixture of 0.20 gm (0.83 mMol) N,N-dimethyl-8-cyano-1,2,3,4-tetrahydro-2-dibenzofuranamine, 15 gm polyphosphoric acid and sufficient chloroform to facilitate mixing were vigorously stirred together as the reaction was gradually raised to 90° C. The reaction was maintained at this temperature for about 4 hours and was then treated with ice chips. Once fluid, the reaction mixture was poured into a cold solution of 5N aqueous sodium hydroxide. The resulting mixture was extracted with 3×350 mL of chloroform. The chloroform extracts were combined, dried over potassium carbonate and concentrated under reduced pressure to provide 0.144 gm (67%) of the title compound.

EXAMPLE 25

N-(N,N-Dimethyl-1,2,3,4-tetrahydro-2-aminodibenzofur-8-yl)pyridine-N-oxide-4-carboxamide hydrochloride A solution of 0.117 gm (0.51 mMol) N,N-dimethyl-8-amino-1,2,3,4-tetrahydro-2-dibenzofuranamine in 5 mL tetrahydrofuran was added to a mixture of 0.117 gm (0.61 mMol) 1-(3-dimethylaminopropyl)-3-ethylcarbodiimide hydrochloride, 0.082 gm (0.61 mMol) 1-hydroxybenzotriazole hydrate, and 0.085 gm (0.61 mMol) pyridine-N-oxide 4-carboxylic acid in 20 mL dimethylformamide. After stirring for 18 hours at room temperature the reaction mixture was diluted with aqueous potassium carbonate and stirred for an additional hour at room temperature. This mixture was extracted well with chloroform. The organic extracts were combined and concentrated under reduced pressure. The residue was subjected twice to radial chromatography (2 mm, silica gel), eluting with 5% methanol in dichloromethane containing 0.5% ammonium hydroxide. Fractions containing product were combined and concentrated under reduced pressure. The residue was dissolved in chloroform and to this solution was added ethanolic hydrogen chloride to provide 0.107 gm (50%) of the title compound.

MS(m/e): 351(M$^+$) Calculated for $C_{20}H_{21}N_3O_3$-HCl: Theory: C, 61.93; H, 5.72; N, 10.83. Found: C, 61.80; H, 5.75; N, 10.57.

EXAMPLE 26

Alternate Preparation of N-(N,N-Dimethyl-1,2,3,4-tetrahydro-2-aminodibenzofur-8-yl)furan-3-carboxamide hydrochloride Beginning with 0.105 gm (0.35 mMol) of N,N-dimethyl-8-amino-1,2,3,4-tetrahydro-2-dibenzofuranamine dihydrochloride hemihydrate and 0.069 gm (0.53 mMol) furo-3-yl chloride, 0.088 gm (70%) of the title compound were recovered as an off-white solid by the procedure of Example 17.

MS(m/e): 324(M$^+$) Calculated for $C_{19}H_{20}N_2O_3$-HCl-0.67 $H_2O$: Theory: C, 61.21;

H, 5.99; N, 7.51. Found: C, 60.77; H, 5.61; N, 7.31.

EXAMPLE 27

N,N-dimethyl-8-hydroxy-1,2,3,4-tetrahydro-2-dibenzofuranamine

A solution of 0.332 gm (1.44 mMol) N,N-dimethyl-8-amino-1,2,3,4-tetrahydro-2-dibenzofuranamine in 5 mL concentrated hydrochloric acid and 5 mL water was cooled to −10° C. To this solution was added a solution of 0.109 gm (1.58 mMol) sodium nitrite in 10 mL water dropwise. The resulting solution was stirred for 1 hour and was then added to 10 mL concentrated sulfuric acid. This mixture was stirred at reflux for 4 hours. The reaction mixture was poured over ice and the solution made basic by the addition of aqueous potassium carbonate. The solution was then extracted well with chloroform containing 10% isopropanol. The organic extracts were combined, dried over potassium carbonate and concentrated under reduced pressure. The residue was subjected to radial chromatography (silica gel, 2 mm). Fractions containing product were combined and concentrated under reduced pressure to provide 0.121 gm (36%) of the title compound as an off-white foam.

MS(m/e): 231(M$^+$) Calculated for $C_{14}H_{17}NO_2$: Theory: C, 72.70; H, 7.41; N, 6.06. Found: C, 72.85; H, 7.27; N, 5.98.

EXAMPLE 28

8-nitro-1,2,3,4-tetrahydro-2-dibenzofuranamine

Beginning with 4-(phthalimid-1-yl)cyclohexanone, 8-nitro-2-(phthalimid-1-yl)dibenzofuranamine was prepared by the procedure described in Example 1. A mixture of 5.50 gm (15.2 mMol) 8-nitro-2-(phthalimid-1-yl)dibenzofuranamine, 100 mL hydrazine hydrate, 150 mL ethanol and 50 mL water was stirred at room temperature for 18 hours. The reaction mixture was concentrated under reduced pressure. The residue was treated with potassium carbonate and then extracted with chloroform. The organic phases were combined and concentrated under reduced pressure. The residue was subjected to silica gel chromatography. Fractions containing product were combined and concentrated under reduced pressure to provide 0.59 gm (92%) of the title compound as a yellow oil.

EXAMPLE 29

8-amino-1,2,3,4-tetrahydro-2-diethylaminodibenzofuran dihydrochloride

A mixture of 0.88 gm (3.79 mMol) 8-nitro-1,2,3,4-tetrahydro-2-dibenzofuranamine, 0.89 gm (5.68 mMol) iodoethane and 1.58 gm (11.4 mMol) potassium carbonate in 50 mL acetone was heated at reflux for 3 hours. The reaction mixture was concentrated under reduced pressure and the residue dissolved in water. This mixture was extracted well with chloroform. The organic phases were combined, dried over potassium carbonate and concentrated under reduced pressure. The residue was subjected to radial chromatography (silica gel, 2 mm). Fractions containing product were combined and concentrated under reduced pressure to provide 0.49 gm (45%) 8-nitro-1,2,3,4-tetrahydro-2-diethylaminodibenzofuran as a yellow oil.

A mixture of 0.48 gm (1.66 mMol) 8-nitro-1,2,3,4-tetrahydro-2-diethylaminodibenzofuran and 0.20 gm 5% platinum on carbon in 250 mL ethanol was hydrogenated at 40 p.s.i. at room temperature for 18 hours. The reaction mixture was filtered and the filtrate concentrated under reduced pressure. The residue was dissolved in dichloromethane, dried over potassium carbonate and concentrated under reduced pressure. This residue was again dissolved in dichloromethane and the solution treated with hydrogen chloride. The precipitate which formed was isolated and dried to provide 0.49 gm (89%) of the title compound as a colorless solid.

EXAMPLE 30

8-amino-1,2,3,4-tetrahydro-2-dipropylaminodibenzofuran hydrochloride

Beginning with 0.88 gm (3.79 mMol) 8-nitro-1,2,3,4-tetrahydro-2-dibenzofuranamine and 1-iodopropane, 0.49 gm (42%) of the title compound was recovered as an off-white solid by the procedure of Example 29.

EXAMPLE 31

N-(N,N-Diethyl-1,2,3,4-tetrahydro-2-aminodibenzofur-8-yl)-4-fluorobenzamide hydrochloride Beginning with 0.100 gm (0.30 mMol) 8-amino-1,2,3,4-tetrahydro-2-diethylaminodibenzofuran and 0.052 gm (0.33 mMol) 4-fluorobenzoyl chloride, 0.088 gm (70%) of the title compound were recovered as an off-white solid by the procedure described in Example 17.

MS(m/e): 380(M$^+$) Calculated for $C_{23}H_{25}N_2O_2F \cdot HCl$: Theory: C, 66.26; H, 6.29; N, 6.72. Found: C, 66.14; H, 6.40; N, 6.79.

EXAMPLE 32

N-(N,N-Diethyl-1,2,3,4-tetrahydro-2-aminodibenzofur-8-yl)isonicotinamide dihydrochloride Beginning with 0.100 gm (0.30 mMol) 8-amino-1,2,3,4-tetrahydro-2-diethylaminodibenzofuran and 0.059 gm (0.33 mMol) isonicotinoyl chloride hydrochloride, 0.068 gm (52%) of the title compound were recovered as a yellow solid by the procedure described in Example 17.

MS(m/e): 363(M$^+$) Calculated for $C_{22}H_{25}N_3O_2 \cdot 2HCl$: Theory: C, 60.25; H, 6.24; N, 9.63. Found: C, 60.69; H, 6.06; N, 9.59.

EXAMPLE 33

N-(N,N-Diethyl-1,2,3,4-tetrahydro-2-aminodibenzofur-8-yl)-3-furamide hydrochloride Beginning with 0.100 gm (0.30 mMol) 8-amino-1,2,3,4-tetrahydro-2-diethylaminodibenzofuran and 0.052 gm (0.40 mMol) furan-3-carbonyl chloride, 0.081 gm (69%) of the title compound were recovered as an off-white solid by the procedure described in Example 17.

MS(m/e): 352(M$^+$) Calculated for $C_{21}H_{24}N_2O_3 \cdot HCl$: Theory: C, 64.86; H, 6.48; N, 7.20. Found: C, 64.73; H, 6.22; N, 7.29.

EXAMPLE 34

N-(N,N-Dipropyl-1,2,3,4-tetrahydro-2-aminodibenzofur-8-yl)-4-fluorobenzamide hydrochloride Beginning with 0.072 gm (0.20 mMol) 8-amino-1,2,3,4-tetrahydro-2-dipropylaminodibenzofuran and 0.032 gm (0.20 mMol) 4-fluorobenzoyl chloride, 0.078 gm (87%) of the title compound were recovered as an off-white solid by the procedure described in Example 17.

MS(m/e): 408(M$^+$) Calculated for $C_{25}H_{29}N_2O_2F \cdot HCl$: Theory: C, 67.48; H, 6.80; N, 6.30. Found: C, 67.26; H, 6.68; N, 6.05.

EXAMPLE 35

N-(N,N-Dipropyl-1,2,3,4-tetrahydro-2-aminodibenzofur-8-yl)isonicotinamide dihydrochloride Beginning with 0.072 gm (0.20 mMol) 8-amino-1,2,3,4-tetrahydro-2-dipropylaminodibenzofuran and 0.054 gm (0.30 mMol) isonicotinoyl chloride hydrochloride, 0.075 gm (81%) of the title compound were recovered as a yellow solid by the procedure described in Example 17.

MS(m/e): 391(M$^+$)

EXAMPLE 36

N-(N,N-Dipropyl-1,2,3,4-tetrahydro-2-aminodibenzofur-8-yl)-3-furamide hydrochloride Beginning with 0.072 gm (0.20 mMol) 8-amino-1,2,3,4-tetrahydro-2-dipropylaminodibenzofuran and 0.026 gm (0.20 mMol) furan-3-carbonyl chloride, 0.064 gm (84%) of the title compound were recovered as a white foam by the procedure described in Example 17.
MS(m/e): 380(M$^+$) Calculated for $C_{23}H_{28}N_2O_3$-HCl: Theory: C, 66.26; H, 7.01; N, 6.72. Found: C, 66.08; H, 6.97; N, 6.76.

EXAMPLE 37

N,N-Dimethyl-8-ethoxycarbonyl-1,2,3,4-tetrahydro-2-dibenzofuranamine
O-(4-ethoxycarbonylphenyl)-4-dimethylcyclohexanone oxime Beginning with 0.45 gm (2.88 mMol) 4-dimethylaminocyclohexanone oxime and 0.53 gm (3.17 mMol) ethyl 4-fluorobenzoate, 0.72 gm (82%) of the desired oxime ether were recovered as a tan solid by the procedure described in Example 1.

MS(m/e): 304(M$^+$)

Cyclization

Beginning with 0.70 gm (2.30 mMol) of the oxime ether and 50 mL formic acid, 0.48 gm (73%) of the title compound were recovered as a white crystalline solid by the procedure described in Example 1.

EXAMPLE 38

N,N-Dimethyl-8-carboxy-1,2,3,4-tetrahydro-2-dibenzofuranamine

A mixture of 0.21 gm (0.73 mMol) N,N-dimethyl-8-ethoxycarbonyl-1,2,3,4-tetrahydro-2-dibenzofuranamine and 25 mL 2N sodium hydroxide in 25 ml tetrahydrofuran was stirred at 35° C. for 18 hours. The reaction mixture was cooled to room temperature and washed with dichloromethane. The aqueous phase was adjusted to pH~7, saturated with sodium chloride, and then extracted well with chloroform containing 10% isopropanol. Organic extracts were combined and concentrated under reduced pressure to provide a white solid which was taken up in hydrochloric acid. The colorless crystalline precipitate which formed was filtered and dried to provide 0.098 ggm (55%) of the title compound.

MS(m/e): 259(M$^+$)

EXAMPLE 39

N-(pyridin-3-yl)-2-dimethylamino-1,2,3,4-tetrahydrodibenzofuran-8-carboxamide

Beginning with 0.17 gm (0.57 mMol) N,N-dimethyl-8-carboxy-1,2,3,4-tetrahydro-2-dibenzofuranamine and 0.06 gm (0.63 mMol) 3-aminopyridine, 0.083 gm (44%) of the title compound were recovered as an off-white foam by the procedure described in Example 25.

MS(m/e): 336(M+1) Calculated for $C_{20}H_{21}N_3O_2$: Theory: C, 71.62; H, 6.31; N, 12.53. Found: C, 71.88; H, 6.41; N, 12.79.

General Procedure for the Coupling of Amines with 2-dimethylamino-1,2,3,4-tetrahydrodibenzofuran-8-carbonyl chloride A mixture of 8-carboxy-2-dimethylamino-1,2,3,4-tetrahydrodibenzofuran and thionyl chloride is stirred at room temperature until homogeneous. The reaction mixture is concentrated under reduced pressure to provide the corresponding acid chloride. One equivalent of acid chloride, 2 equivalents of the appropriate amine, and 3 equivalents of piperidinomethylpolystyrene in chloroform are stirred at room temperature for 18 hours. An isocyanate resin is added to remove unreacted amine and the mixture is stirred at room temperature for 4 hours. The resins are removed by filtration and the product is isolated by evaporation of solvent. This procedure is illustrated by Examples 40–44.

EXAMPLE 40

N-(methyl)-2-dimethylamino-1,2,3,4-tetrahydrodibenzofur-an-8-carboxamide

Beginning with 0.011 gm (0.04 mMol) 2-dimethylamino-1,2,3,4-tetrahydrodibenzofuran-8-carbonyl chloride and 0.08 mMol methylamine, 0.0023 gm (20%) of the title compound were recovered.

MS(m/e): 273(M+1)

EXAMPLE 41

N-(ethyl)-2-dimethylamino-1,2,3,4-tetrahydrodibenzofuran-8-carboxamide

Beginning with 0.011 gm (0.04 mMol) 2-dimethylamino-1,2,3,4-tetrahydrodibenzofuran-8-carbonyl chloride and 0.08 mMol ethylamine, 0.0037 gm (33%) of the title compound were recovered.

MS(m/e): 287(M+1)

EXAMPLE 42

N-(cyclopropyl)-2-dimethylamino-1,2,3,4-tetrahydrodibenzofuran-8-carboxamide

Beginning with 0.011 gm (0.04 mMol) 2-dimethylamino-1,2,3,4-tetrahydrodibenzofuran-8-carbonyl chloride and 0.08 mMol cyclopropylamine, 0.004 gm (32%) of the title compound were recovered.

MS(m/e): 299(M+1)

EXAMPLE 43

N-(4-fluorophenyl)-2-dimethylamino-1,2,3,4-tetrahydrodibenzofuran-8-carboxamide

Beginning with 0.011 gm (0.04 mMol) 2-dimethylamino-1,2,3,4-tetrahydrodibenzofuran-8-carbonyl chloride and 0.08 mMol 4-fluoroaniline, 0.001 gm (7%) of the title compound were recovered.

MS(m/e): 353(M+1)

EXAMPLE 44

N-(pyridin-4-yl)-2-dimethylamino-1,2,3,4-tetrahydrodibenzofuran-8-carboxamide

Beginning with 0.011 gm (0.04 mMol) 2-dimethylamino-1,2,3,4-tetrahydrodibenzofuran-8-carbonyl chloride and 0.08 mMol 4-aminopyridine, 0.0052 gm (37%) of the title compound were recovered.

MS(m/e): 336(M+1)

EXAMPLE 45

2-dimethylamino-8-(N,N-dimethyl)aminosulfonyl-1, 2,3,4-tetrahydrodibenzofuran hydrochloride O-(4-(N,N-dimethyl)aminosulfonylphenyl)-4-dimethylcyclohexanone oxime Beginning with 0.104 gm (0.67 mMol) 4-dimethylaminocyclohexanone oxime and 0.124 gm (0.61 mMol) N,N-dimeth-yl-4-fluorophenylsulfonamide, 0.135 gm (65%) of the desired oxime ether were recovered as a crystalline solid by the procedure described in Example 1.

Cyclization

Beginning with 0.135 gm (0.40 mMol) of the oxime ether and 10 mL formic acid, 0.088 gm (61%) of the title compound were recovered as a white solid by the procedure described in Example 1.

MS(m/e): 322($M^+$) Calculated for $C_{16}H_{22}N_2O_3S$-HCl: Theory: C, 53.55; H, 6.46; N, 7.81. Found: C, 53.48; H, 6.54; N, 7.61.

EXAMPLE 46

2-dimethylamino-8-(N-methyl)aminosulfonyl-1,2,3, 4-tetrahydrodibenzofuran hydrochloride O-(4-(N-methyl-N-(4-methoxybenzyl))aminosulfonylphenyl)-4-dimethylcyclohexanone oxime Beginning with 0.313 gm (2.0 mMol) 4-dimethylaminocyclohexanone oxime and 0.681 gm (2.2 mMol) N-methyl-N-(4-methoxy)benzyl-4-fluorophenylsulfonamide, 0.781 gm (90%) of the desired oxime ether were recovered as a pale yellow crystalline solid by the procedure described in Example 1.

Cyclization

Beginning with 0.750 gm (1.74 mMol) of the oxime ether and 20 mL formic acid, 0.135 gm (25%) of the title compound were recovered as an off-white solid by the procedure described in Example 1.

MS(m/e): 308($M^+$) Calculated for $C_{15}H_{20}N_2O_3S$-HCl: Theory: C, 58.42; H, 6.54; N, 9.08. Found: C, 58.57; H, 6.64; N, 8.93.

EXAMPLE 47

2-dimethylamino-8-(N-(4-fluorophenyl)) aminosulfonyl-1,2,3,4-tetrahydrodibenzofuran O-(4-(N-(4-fluorophenyl)-N-(4-methoxybenzyl))aminosulfonylphenyl)-4-dimethylcyclohexanone oxime Beginning with 0.78 gm (5.0 mMol) 4-dimethylaminocyclohexanone oxime and 2.14 gm (5.5 mMol) N-(4-fluoro)-phenyl-N-(4-methoxy)benzyl-4-fluorophenylsulfonamide, 1.13 gm (43%) of the desired oxime ether were recovered as an off-white solid by the procedure described in Example 1.

MS(m/e): 525($M^+$)

Cyclization

Beginning with 1.13 gm (2.15 mMol) of the oxime ether and 20 mL formic acid, 0.610 gm (73%) of the title compound were recovered as an off-white solid by the procedure described in Example 1.

MS(m/e): 388($M^+$) Calculated for $C_{20}H_{21}NO_3S$: Theory: C, 61.84; H, 5.45; N, 7.21. Found: C, 62.01; H, 5.50; N, 7.09.

To demonstrate the use of the compounds of this invention in the treatment of migraine, their ability to bind to the 5-$HT_{1F}$ receptor subtype was determined. The ability of the compounds of this invention to bind to the 5-$HT_{1F}$ receptor subtype was measured essentially as described in N. Adham, et al., *Proceedings of the National Academy of Sciences* (*USA*), 90, 408–412 (1993).

Membrane Preparation: Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-$HT_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 μL of buffer (50 mM Tris, 10 mM $MgCl_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. All of the compounds of the invention exemplified exhibited an $IC_{50}$ at the 5-$HT_{1F}$ receptor of at least 5 μmol.

As was reported by R. L. Weinshank, et al., WO93/14201, the 5-$HT_{1F}$ receptor is functionally coupled to a G-protein as measured by the ability of serotonin and serotonergic drugs to inhibit forskolin stimulated cAMP production in NIH3T3 cells transfected with the 5-$HT_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the National Academy of Sciences* (*USA*), 89,3630–3634 (1992)), and the references cited therein.

Measurement of cAMP Formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% $CO_2$. Drug dose-effect curves were then conducted by adding 6 different final concentrations of drug, followed immediately by the addition of forskolin (10 μM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 μM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software.

The discovery that the pain associated with migraine and associated disorders is inhibited by agonists of the $5-HT_{1F}$ receptor required the analysis of data from diverse assays of pharmacological activity. To establish that the $5-HT_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the $5-HT_{1F}$ receptor subtype was performed as described supra. For comparison purposes, the binding affinities of compounds to the $5-HT_{1D\alpha}$, $5-HT_{1D\beta}$, $5-HT_{1E}$ and $5-HT_{1F}$ receptors were also determined as described supra, except that different cloned receptors were employed in place of the $5-HT_{1F}$ receptor clone employed therein. The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I

3-[2-(dimethylamino)ethyl]-N-methyl-1H-indole-5-methanesulfonamide butane-1, 4-dioate (1:1)
(Sumatriptan succinate)

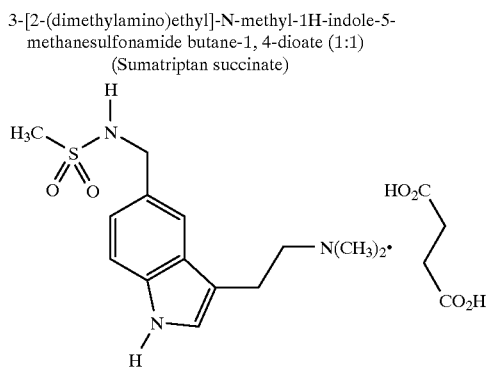

Sumatriptan succinate is commercially available as Imitrex™ or may be prepared as described in U.S. Pat. No. 5,037,845, issued Aug. 6, 1991, which is herein incorporated by reference.

Compound II 5-fluoro-3-<1-<2-<1-methyl-1H-pyrazol-4-yl>ethyl>-4-piperidinyl>-1H-indole hydrochloride

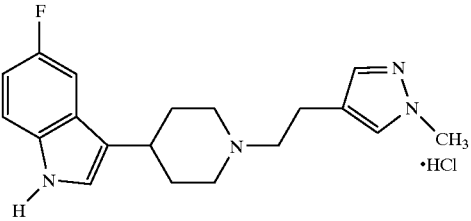

Compound III 5-hydroxy-3-(4-piperidinyl)-1H-indole oxalate

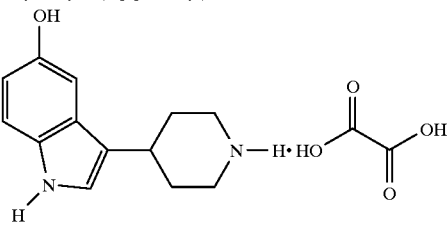

Compound IV 8-chloro-2-diethylamino-1, 2, 3, 4-tetrahydronaphthalene hydrochloride

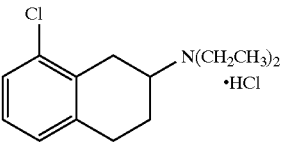

Compound V 6-hydroxy-3-dimethylamino-1, 2, 3, 4-tetrahydrocarbazole

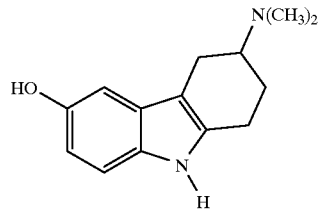

Compounds II–V are described in U.S. Pat. No. 5,521,196, issued May 28, 1996, which is herein incorporated by reference in its entirety.

Binding Assays

The binding affinities of compounds for various serotonin receptors were determined essentially as described above except that different cloned receptors are employed in place of the $5-HT_{1F}$ receptor clone employed therein. The results of these binding experiments are summarized in Table II.

TABLE II

BINDING TO SEROTONIN (5-HT$_1$) RECEPTOR SUBTYPES (K$_i$ nM)

| Compound | 5-HT$_{1D\alpha}$ | 5-HT$_{1D\beta}$ | 5-HT$_{1E}$ | 5-HT$_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-HT$_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 $\mu$m steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% (ID$_{50}$) was approximated. This data is presented in Table III.

TABLE III

Inhibition of Protein Extravasation (ID$_{50}$ mMol/kg)

| Compound | i.v. ID$_{50}$ (mMol/kg) |
|---|---|
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the 5-HT$_{1D\alpha}$, 5-HT$_{1D\beta}$, 5-HT$_{1E}$ and 5-HT$_{1F}$ receptors was plotted against their ID$_{50}$ in the protein extravasation model. A linear regression analysis was performed on each set of data and a correlation factor, R$^2$, calculated. The results of this analysis are summarized in Table IV.

TABLE IV

Correlation Factor (R$^2$) for Specific 5-HT$_1$ Subtype Binding Affinity vs Inhibition of Protein Extravasation

| 5-HT$_1$ Subtype | Correlation Factor (R$^2$) |
|---|---|
| 5-HT$_{1D\alpha}$ | 0.07 |
| 5-HT$_{1D\beta}$ | 0.001 |
| 5-HT$_{1E}$ | 0.31 |
| 5-HT$_{1F}$ | 0.94 |

An ideally linear relationship would generate a correlation factor of 1.0, indicating a cause and effect relationship between the two variables. The experimentally determined correlation factor between inhibition of neuronal protein extravasation and 5-HT$_{1F}$ binding affinity is 0.94. This nearly ideal dependence of the ID$_{50}$ in the protein extravasation model on binding affinity to the 5-HT$_{1F}$ receptor clearly demonstrates that the 5-HT$_{1F}$ receptor mediates the inhibition of protein extravasation resulting from stimulation of the trigem-inal ganglia.

Sumatriptan exhibits low bioavailability and relatively short duration of action. Its affinity for a number of serotonin receptor subtypes gives rise to undesirable side effects, particularly vasoconstriction, which severely limits its utility in the treatment of migraine. The compounds of this invention, however, are highly bioavailable through several routes of administration including, but not limited to, oral, buccal, intravenous, subcutaneous and rectal. They exhibit a rapid onset and long duration of action, typically requiring only a single dose per day to maintain therapeutic levels. Since compounds of this invention are potent agonists of the 5-HT$_{1F}$ receptor, extremely low doses are required to maintain therapeutic levels. Additionally, due to the high selectivity of compounds of this invention for the 5-HT$_{1F}$ receptor, complications due to vasoconstriction are avoided. Compounds of this invention also inhibit protein extravasation if administered prior or subsequent to stimulation of the trigeminal ganglia. As such, they may either be administered prophylactically to prevent a migraine attack, or be administered prior to or during a migraine attack to alleviate pain.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 24 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 25 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A compound of the Formula I

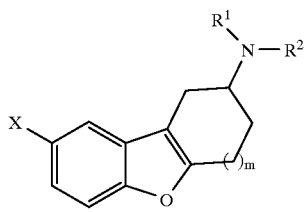

wherein:
R$^1$ and R$^2$ are independently hydrogen, C$_1$–C$_4$ alkyl, benzyl, or α-methyl-4-nitrobenzyl;
X is —NHC(O)R$^3$, or —C(O)R$^6$;
R$^3$ is an optionally substituted furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, isoquinolinyl, benzofuranyl, benzo[b]thienyl, or 1H-indolyl bonded through any available ring carbon atom;
R$^6$ is —NHR$^8$;
R$^8$ is an optionally substituted furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, isoquinolinyl, benzofuranyl, benzo[b]thienyl, or 1H-indolyl bonded through any available ring carbon atom; and
m is 1 or 2; or pharmaceutically acceptable salts thereof.

2. A compound of claim 1 where m is 1.
3. A compound of claim 1 where X is —NHC(O)R$^3$.
4. A compound of claim 3 where R$^3$ is pyridinyl.
5. A compound of claim 1 where X is —C(O)R$^6$.
6. A compound of claim 5 where R$^6$ is —NHR$^8$.
7. A method of increasing activation of the 5-HT$_{1F}$ receptor in a mammal comprising administering to a mammal in need of said activation an effective amount of a compound of claim 1.
8. A method of claim 7 where the mammal is a human.
9. A pharmaceutical formulation comprising an effective amount of a compound of Formula

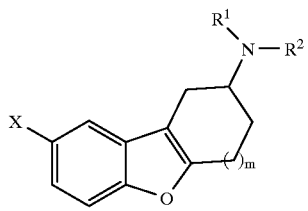

wherein:
R$^1$ and R$^2$ are independently hydrogen, C$_1$–C$_4$ alkyl, benzyl, or α-methyl-4-nitrobenzyl;
X is —NHC(O)R$^3$, or —C(O)R$^6$;
R$^3$ is an optionally substituted furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, isoquinolinyl, benzofuranyl, benzo[b]thienyl, or 1H-indolyl bonded through any available ring carbon atom;
R$^6$ is —NHR$^8$;
R$^8$ is an optionally substituted furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, isoquinolinyl, benzofuranyl, benzo[b]thienyl, or 1H-indolyl bonded through any available ring carbon atom; and
m is 1 or 2; or pharmaceutically acceptable salts thereof, in combination with a suitable pharmaceutical carrier, diluent, or excipient.

10. A compound of claim 6, where R8 is pyridin-3-yl.
11. The compound N-(pyridin-3-yl)-2-dimethylamino-1,2,3,4-tetrahydrodibenzofuran-8-carboxamide or a pharmaceutically acceptable salt thereof.
12. The compound N-(pyridin-3-yl)-2-dimethylamino-1,2,3,4-tetrahydrodibenzofuran-8-carboxamide hydrochloride.

* * * * *